(12) United States Patent
Korytko

(10) Patent No.: US 11,065,376 B2
(45) Date of Patent: Jul. 20, 2021

(54) PLASMAPHERESIS CENTRIFUGE BOWL

(71) Applicant: Haemonetics Corporation, Boston, MA (US)

(72) Inventor: Taylor Korytko, Newton, MA (US)

(73) Assignee: HAEMONETICS CORPORATION, Boston, MA (US)

( * ) Notice: Subject to any disclaimer, the term of this patent is extended or adjusted under 35 U.S.C. 154(b) by 701 days.

(21) Appl. No.: 15/935,476

(22) Filed: Mar. 26, 2018

(65) Prior Publication Data

US 2019/0290824 A1   Sep. 26, 2019

(51) Int. Cl.
| | |
|---|---|
| *A61M 1/34* | (2006.01) |
| *A61M 1/36* | (2006.01) |
| *B04B 5/04* | (2006.01) |
| *B04B 7/08* | (2006.01) |

(52) U.S. Cl.
CPC ........ *A61M 1/3496* (2013.01); *A61M 1/3696* (2014.02); *B04B 5/0442* (2013.01); *A61M 1/3403* (2014.02); *A61M 2202/0415* (2013.01); *A61M 2205/3306* (2013.01); *B04B 7/08* (2013.01); *B04B 2005/0464* (2013.01)

(58) Field of Classification Search
CPC .............. A61M 1/3496; A61M 1/3696; A61M 2202/0415; B04B 2005/0464; B04B 5/0442

See application file for complete search history.

(56) References Cited

U.S. PATENT DOCUMENTS

| | | | |
|---|---|---|---|
| 1,025,059 | A | 4/1912 | Hatton et al. |
| 1,611,725 | A | 12/1926 | Degerth et al. |
| 2,087,778 | A | 7/1937 | Nelin |
| 2,750,107 | A | 6/1956 | More |
| 2,792,172 | A | 5/1957 | Tait |

(Continued)

FOREIGN PATENT DOCUMENTS

| | | |
|---|---|---|
| CN | 2927990 Y | 8/2007 |
| CN | 102046224 A | 5/2011 |

(Continued)

OTHER PUBLICATIONS

International Search Report and Written Opinion of International Application No. PCT/US2019/023100, filed Mar. 20, 2019, dated Jun. 14, 2019 and dated Aug. 19, 2019 by Authorized Officer Teresa Mata Vicente, European Patent Office.

*Primary Examiner* — Ariana Zimbouski
(74) *Attorney, Agent, or Firm* — McCarter & English, LLP; Jonathan C. Lovely

(57) ABSTRACT

A plasmapheresis bowl for the separation and collection of plasma includes a core and a feed tube that increase the bowl efficiency and reduce foaming within the plasma. The core may have a cylindrical body and a ledge located within the interior of the core. The ledge extends radially inward from the core and defines, at least partially, a collection chamber within the plasmapheresis bowl. The core also has ribs that extend above the top of core body and create flow paths that allow fluid to enter the interior of the cylindrical body and collection chamber. The feed tube has a flow path extending through it that fluidly connects an inlet port on the plasmapheresis centrifuge. A first skirt member on the feed tube has a smooth angled surface that helps to reduce foaming.

43 Claims, 14 Drawing Sheets

(56) References Cited

U.S. PATENT DOCUMENTS

| | | | |
|---|---|---|---|
| 3,145,713 A | 8/1964 | Latham, Jr. | |
| 3,409,213 A | 11/1968 | Latham, Jr. | |
| 3,565,330 A | 2/1971 | Latham, Jr. | |
| 3,655,058 A | 4/1972 | Novak | |
| 3,774,840 A | 11/1973 | Boatright | |
| 3,955,755 A | 5/1976 | Breillatt, Jr. et al. | |
| 4,014,497 A | 3/1977 | Spiewok et al. | |
| 4,040,965 A | 8/1977 | Kohlheb | |
| 4,086,924 A | 5/1978 | Latham, Jr. | |
| 4,140,268 A | 2/1979 | Lacour | |
| 4,300,717 A | 11/1981 | Latham, Jr. | |
| 4,425,114 A | 1/1984 | Schoendorfer et al. | |
| 4,466,888 A | 8/1984 | Verkaart | |
| 4,534,863 A | 8/1985 | Bacon et al. | |
| 4,684,361 A | 8/1987 | Feldman et al. | |
| 4,692,136 A | 9/1987 | Feldman et al. | |
| 4,713,176 A | 12/1987 | Schoendorfer et al. | |
| 4,729,759 A | 3/1988 | Krook et al. | |
| 4,740,202 A | 4/1988 | Stacey et al. | |
| 4,740,313 A | 4/1988 | Schoendorfer et al. | |
| 4,755,300 A | 7/1988 | Fischel et al. | |
| 4,767,396 A | 8/1988 | Powers | |
| 4,795,419 A | 1/1989 | Yawn et al. | |
| 4,795,448 A | 1/1989 | Stacey et al. | |
| 4,806,247 A | 2/1989 | Schoendorfer et al. | |
| 4,808,307 A | 2/1989 | Fischel et al. | |
| 4,859,333 A | 8/1989 | Panzani | |
| 4,869,812 A | 9/1989 | Schoendorfer et al. | |
| 4,871,462 A | 10/1989 | Fischel et al. | |
| 4,876,013 A | 10/1989 | Shmidt et al. | |
| 4,889,524 A | 12/1989 | Fell et al. | |
| 4,943,273 A | 7/1990 | Pages | |
| 4,983,158 A | 1/1991 | Headley | |
| 4,994,188 A | 2/1991 | Prince | |
| 5,045,048 A | 9/1991 | Kaleskas et al. | |
| 5,100,372 A | 3/1992 | Headley | |
| 5,100,564 A | 3/1992 | Pall et al. | |
| 5,194,145 A | 3/1993 | Schoendorfer | |
| 5,254,248 A | 10/1993 | Nakamura | |
| 5,387,174 A | 2/1995 | Rochat | |
| 5,403,272 A | 4/1995 | Deniega et al. | |
| 5,405,308 A | 4/1995 | Headley et al. | |
| 5,431,814 A | 7/1995 | Jorgensen | |
| 5,462,667 A | 10/1995 | Wollinsky et al. | |
| 5,464,536 A | 11/1995 | Rogers | |
| 5,478,479 A | 12/1995 | Herrig | |
| 5,494,592 A | 2/1996 | Latham, Jr. et al. | |
| 5,514,070 A | 5/1996 | Pages | |
| 5,551,941 A | 9/1996 | Howell | |
| 5,585,007 A | 12/1996 | Antanavich et al. | |
| 5,607,579 A | 3/1997 | Latham, Jr. et al. | |
| 5,649,903 A | 7/1997 | Deniega et al. | |
| 5,651,766 A | 7/1997 | Kingsley et al. | |
| 5,656,163 A | 8/1997 | Brown | |
| 5,720,921 A | 2/1998 | Meserol | |
| 5,733,446 A | 3/1998 | Holm | |
| 5,738,792 A | 4/1998 | Schoendorfer | |
| 5,762,791 A | 6/1998 | Deniega et al. | |
| 5,779,660 A | 7/1998 | Kingsley et al. | |
| 5,783,085 A | 7/1998 | Fischel | |
| 5,792,351 A | 8/1998 | Wehrle et al. | |
| 5,853,382 A | 12/1998 | Kingsley et al. | |
| 5,882,289 A * | 3/1999 | Sakota | B04B 5/0442 494/41 |
| 5,919,125 A | 7/1999 | Berch | |
| 6,099,491 A | 8/2000 | Headley et al. | |
| 6,224,531 B1 | 5/2001 | Frehland et al. | |
| 6,464,624 B2 | 10/2002 | Pages | |
| 6,629,919 B2 * | 10/2003 | Egozy | B04B 5/0442 494/36 |
| 6,743,192 B1 | 6/2004 | Sakota et al. | |
| 7,037,428 B1 | 5/2006 | Robinson et al. | |
| 2001/0006810 A1 | 7/2001 | Brown | |
| 2002/0058030 A1 | 5/2002 | Monroy et al. | |
| 2003/0125881 A1 | 7/2003 | Ryan | |
| 2003/0181305 A1 | 9/2003 | Briggs et al. | |
| 2003/0233064 A1 | 12/2003 | Arm et al. | |
| 2004/0127840 A1 | 7/2004 | Gara et al. | |
| 2006/0199720 A1* | 9/2006 | Juan | B04B 7/00 494/41 |
| 2006/0226090 A1 | 10/2006 | Robinson et al. | |
| 2007/0012623 A1 | 1/2007 | Robinson et al. | |
| 2009/0259163 A1 | 10/2009 | Pages et al. | |
| 2009/0259164 A1 | 10/2009 | Pages et al. | |
| 2012/0040443 A1* | 2/2012 | Wase | C11B 1/04 435/271 |
| 2013/0089917 A1* | 4/2013 | Kessler | C12M 27/10 435/261 |
| 2013/0310241 A1 | 11/2013 | Kabaha et al. | |
| 2013/0331252 A1* | 12/2013 | Brunner | A61M 1/3696 494/38 |
| 2014/0045672 A1 | 2/2014 | Galavotti et al. | |
| 2014/0128239 A1 | 5/2014 | Murphy et al. | |
| 2015/0273132 A1 | 10/2015 | Ragusa et al. | |

FOREIGN PATENT DOCUMENTS

| | | |
|---|---|---|
| EP | 257755 A1 | 3/1988 |
| EP | 619145 A2 | 10/1994 |
| EP | 664159 A1 | 7/1995 |
| EP | 799645 A1 | 10/1997 |
| EP | 1057534 A1 | 12/2000 |
| GB | 480216 A | 2/1938 |
| JP | 59-6952 A | 1/1984 |
| JP | 59-69166 A | 4/1984 |
| JP | H07-75746 A | 3/1995 |
| JP | H09-104631 A | 4/1997 |
| JP | H09-192215 A | 7/1997 |
| JP | 2000-102603 A | 4/2000 |
| JP | 2006-020756 A | 1/2006 |
| RU | 2534631 C1 | 12/2014 |
| WO | 1990/07383 A1 | 7/1990 |
| WO | 1994/06535 A1 | 3/1994 |
| WO | 94/08721 A1 | 4/1994 |
| WO | 2009/129131 A1 | 10/2009 |
| WO | 2012/137086 A1 | 10/2012 |
| WO | 2014/070209 A1 | 5/2014 |

* cited by examiner

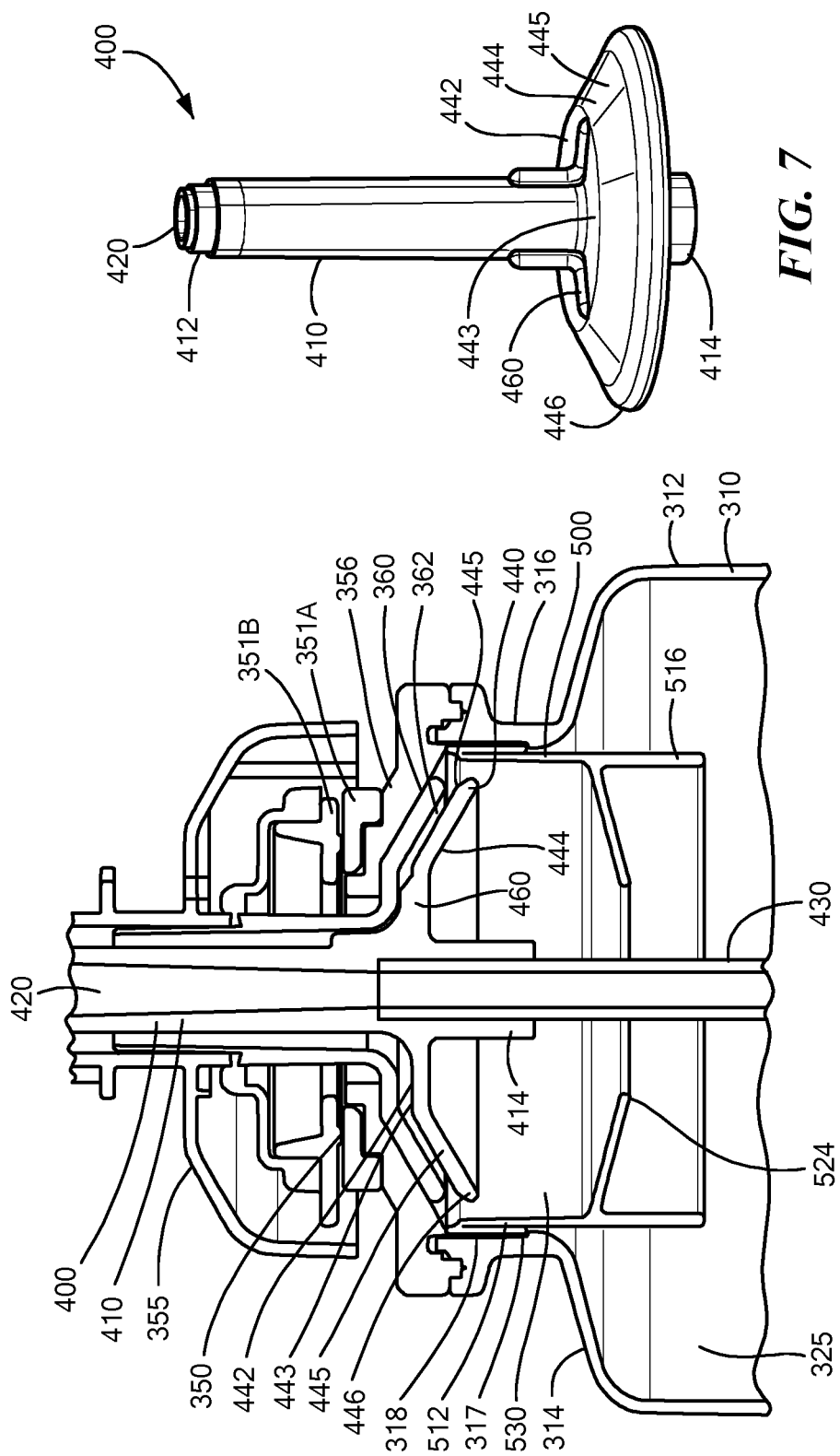

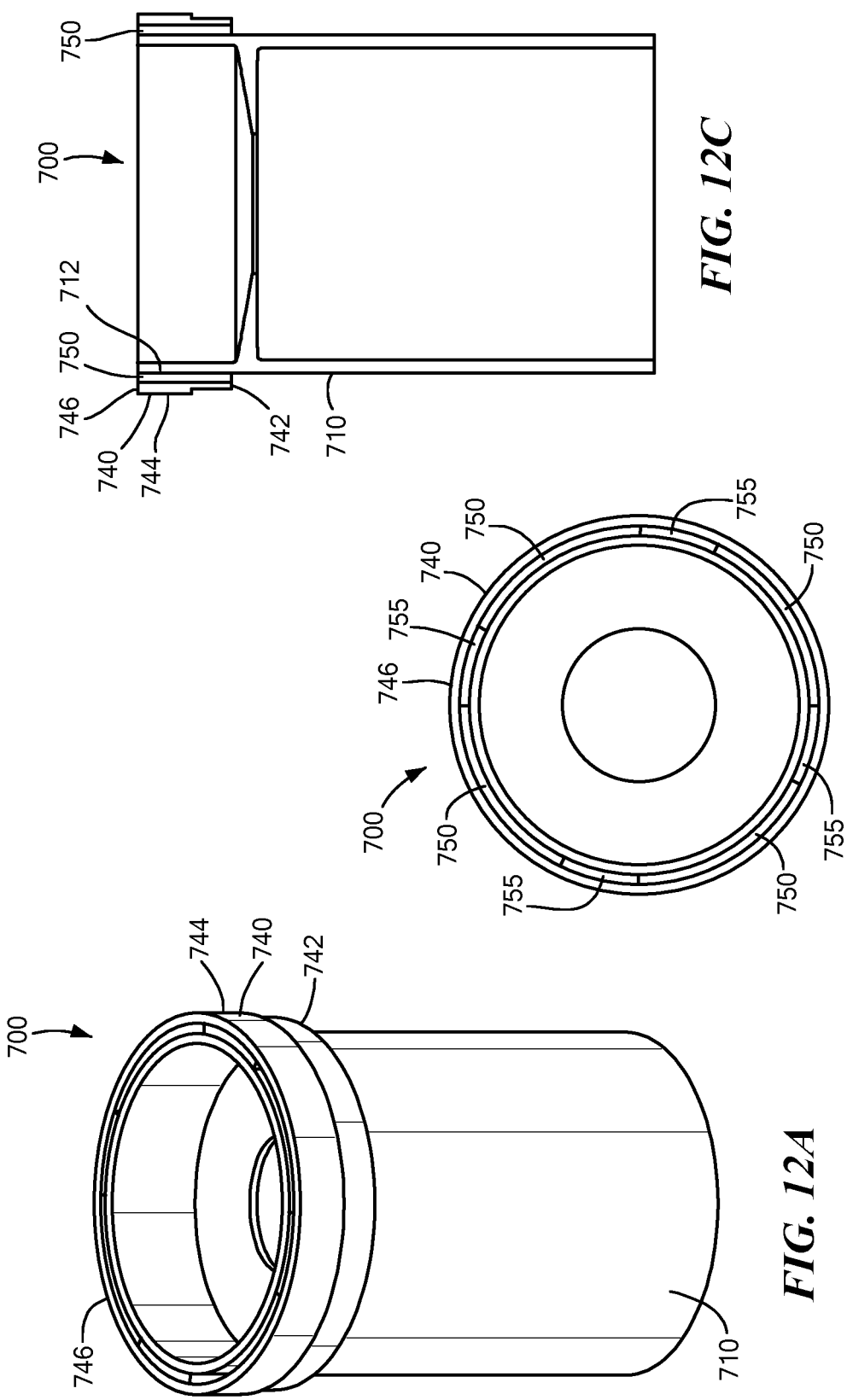

PLASMAPHERESIS CENTRIFUGE BOWL

TECHNICAL FIELD

The present invention relates to systems and methods for blood apheresis, and more particularly centrifuge bowls for collecting a plasma product.

BACKGROUND ART

Apheresis is a procedure in which individual blood components can be separated and collected from whole blood temporarily withdrawn from a subject. Typically, whole blood is withdrawn through a needle inserted into a vein of the subjects arm and into a cell separator, such as a centrifugal bowl. Once the whole blood is separated into its various components, one or more of the components (e.g., plasma) can be removed from the centrifugal bowl. The remaining components can be returned to the subject along with optional compensation fluid to make up for the volume of the removed component. The process of drawing and returning continues until the quantity of the desired component has been collected, at which point the process is stopped. A central feature of apheresis systems is that the processed but unwanted components are returned to the donor. Separated blood components may include, for example, a high density component such as red blood cells, an intermediate density component such as platelets or white blood cells, and a lower density component such as plasma.

Some of the currently available centrifuge bowls are subject to turbulence and shear forces that negatively impact blood component separation and plasma collection. For instance, some prior art centrifuge bowls allow turbulence and shear forces (e.g., generated by spinning fluid contacting an effluent skirt) to be transmitted into the separation chamber of the bowl. This, in turn, disturbs the separation of the cells in the separation chamber, causes a noisy bowl optics signal, and reduces cellular separation from the plasma. Additionally, the turbulence and shear forces may cause foaming within the plasma that is to be collected.

SUMMARY OF THE INVENTION

In accordance with some embodiments of the present invention, a core for a plasmapheresis bowl may include a cylindrical body, a ledge, and a plurality of rib members. The cylindrical body defines the core and an interior of the core. The ledge may be located within the interior of the core between a proximal end and a distal end of the cylindrical body, and may extend radially inward from the inner diameter of the core. The ledge may have a top surface that defines, at least partially, a collection chamber within the plasmapheresis bowl. The ribs may be located on and spaced about a proximal portion of the cylindrical body nearer the proximal end. The ribs may extend above the proximal end of the cylindrical body and create flow paths between them that allow fluid to enter the interior of the cylindrical body and the collection chamber. The plurality of ribs may include three or more ribs (e.g., eight ribs).

In some embodiments, the cylindrical body may have a second portion that is located below the ledge. The second portion may provide a reflective surface for an optical sensor. Additionally, the cylindrical body may have a distal portion located below the second portion that may stabilize fluid within the plasmapheresis bowl (e.g., during processing). The proximal portion may be located above the ledge, and may isolate the collection chamber from a separation region within the plasmapheresis bowl. Additionally or alternatively, the proximal portion may prevent turbulence and shear forces within the collection chamber from reaching the separation region. The inner wall of the proximal portion may define a side wall of the collection chamber.

Each of the plurality of ribs may include a top surface, a bottom surface, and an outer surface. The top surface of at least one of the ribs may interface with a portion of the plasmapheresis bowl to secure the cylindrical body within the plasmapheresis bowl. The bottom surface of at least one of ribs may interface with a mating ledge on a body of the plasmapheresis bowl to locate the core in the plasmapheresis bowl. The outer surface of at least one of ribs may interface with an interior surface of the plasmapheresis bowl (e.g., within the neck portion of the bowl) and create an interference fit between the core and the plasmapheresis bowl.

In some embodiments, the top surface of the ledge may slope downward toward the distal end of the cylindrical body. The ledge may also include a bottom surface that prevents fluid within the interior of the core and below the ledge from entering the collection chamber. The ledge may also include an opening that extends through the ledge. The opening may allow a feed tube of the plasmapheresis bowl to pass through the ledge and allow fluid within the collection chamber to exit the collection chamber when the plasmapheresis bowl is stopped. The opening may be located at the center of the ledge such that it is coaxial with the cylindrical body. The cylindrical body may have a constant outer diameter along a length of the cylindrical body.

In accordance with additional embodiments, a feed tube for a plasmapheresis centrifuge bowl may include a tubular member extending between a proximal portion end and a distal end, and a first skirt member. The tubular member may have a flow path extending through it that fluidly connects an inlet port on the plasmapheresis centrifuge bowl and an interior of the plasmapheresis centrifuge bowl. The first skirt member may extend radially outward from the tubular member and may have (1) a first surface that is generally perpendicular to the tubular member and (2) an angled surface extending radially outward and distally from the first surface. The angled surface may be smooth.

The feed tube may also have at least one spacing rib (e.g., three ribs equally spaced about the skirt member) that is located on the first surface. The spacing rib may space the first skirt member from a second skirt member to create a fluid channel extending between the first skirt member and the second skirt member. The second skirt member may be located on a header assembly of the plasmapheresis centrifuge bowl. The spacing rib(s) may have a first portion that extends along the first surface, and a second portion that extends proximally along at least a portion of the tubular member. A core within the plasmapheresis bowl and the first and second skirts may be configured such that the distance between the inner diameter of a proximal portion of the core and the outer diameter of the first and second skirts is maximized.

The fluid channel may fluidly connect a collection chamber within the plasmapheresis centrifuge bowl with an outlet port on the plasmapheresis centrifuge bowl. The feed tube may also include an extension tube that is connected to the tubular member at the distal end and extends toward a bottom of the plasmapheresis centrifuge bowl. Fluid entering the plasmapheresis centrifuge bowl via the feed tube may be introduced nearer to the bottom of the plasmapheresis centrifuge bowl.

In accordance with further embodiments, a plasmapheresis bowl may include an outer body that is rotatable about a longitudinal axis of the centrifuge bowl. The outer body may have a main body defining an interior cavity, a neck portion extending proximal to the main body, and a shoulder connecting the main body and the neck portion. The bowl may also include a core located within and rotatable with the outer body. The core may have (1) a cylindrical body defining the core and an interior of the core, (2) a ledge, and (3) a plurality of ribs (e.g., eight ribs). The ledge may be located within the interior of the core between a proximal end and a distal end of the cylindrical body, and may extend radially inward from an inner diameter of the core. The ledge may have a top surface that defines, at least partially, a collection chamber within the plasmapheresis bowl. The ribs may be located on and spaced about a proximal portion of the cylindrical body nearer the proximal end of the cylindrical body. The ribs may also extend above the proximal end of the cylindrical body to create flow paths between each of the ribs. The flow paths allow fluid to enter the interior of the cylindrical body and collection chamber.

The bowl may also have a separation region located between the core and the outer body, and rotation of the centrifuge bowl may separate the whole blood within the separation region into a first blood component and a second blood component. Additionally, the bowl may have an inlet port for introducing whole blood into the plasmapheresis bowl, an outlet port for extracting a first blood component out of the centrifuge bowl, a feed tube and a rotary seal. The feed tube may be fluidly connected to and extend distally from the inlet port toward a bottom of the outer body and may introduce the whole blood into the plasmapheresis bowl. The rotary seal may be part of the header assembly which may be attached to the outer body and fluidly couple the inlet port and outlet port to the outer body.

In some embodiments, the cylindrical body of the core may have a second portion located below the ledge and at least a portion of the second portion may provide a reflective surface for an optical sensor. Additionally or alternatively, the cylindrical body may have a distal portion that is located below the second portion and is configured to stabilize fluid within the plasmapheresis bowl. For example, the distal portion of the cylindrical body may be configured to stabilize a plasma layer within the separation region. The inner diameter of a separated plasma later within the separation region may contact the distal portion of the cylindrical body.

The proximal portion may be located above the ledge and may isolate the collection chamber from the separation region. For example the proximal portion may prevent turbulence and shear forces within the collection chamber from reaching the separation region. The inner wall of the proximal portion may define a side wall of the collection chamber.

Each of the plurality of ribs may include a top surface, an outer surface, and a bottom surface. The top surface of at least one rib may interface with a portion of the seal crown to secure the cylindrical body within the plasmapheresis bowl. The outer body may have a mating ledge within the neck portion and the bottom surface of at least one of the ribs may interface with the mating ledge of the plasmapheresis bowl (e.g., to locate the core in the plasmapheresis bowl). The outer surface of at least one rib may interface with an interior surface of the neck portion of the plasmapheresis bowl to create an interference fit between the core and the plasmapheresis bowl.

In further embodiments, the top surface of the ledge may slope downward toward the distal end of the cylindrical body. The bottom surface of the ledge may prevent fluid within the interior of the core and below the ledge from entering the collection chamber. Additionally or alternatively, the ledge may have an opening extending through it. In such embodiments, the feed tube may extend through the opening. The opening may be located at the center of the ledge such that it is coaxial with the cylindrical body. The cylindrical body may have a constant outer diameter along a length of the cylindrical body.

The feed tube may include a tubular member and a first skirt. The tubular member may extend between a proximal end and a distal end of the feed tube, and may have a flow path extending therethrough. The flow path may fluidly connect the inlet port and the interior cavity of the plasmapheresis bowl. The first skirt member may extend radially outward from the tubular member. The first skirt may have first surface that is generally perpendicular to the tubular member and an angled surface extending radially outward and distally from the first surface. The angled surface may be smooth.

In additional embodiments, the feed tube further may include at least one spacing rib (e.g., three ribs that are equally spaced about the skirt member) located on the first surface. The spacing rib(s) may space the first skirt member from a second skirt member to create a fluid channel extending between skirt members. The fluid channel may fluidly connect the collection chamber and the outlet port. The second skirt member may be located on a header assembly of the plasmapheresis centrifuge bowl. The spacing rib(s) may have a first portion that extends along the first surface, and a second portion that extends proximally along at least a portion of the tubular member. The plasmapheresis bowl and the first and second skirts may be configured such that the distance between the inner diameter of the proximal portion of the core wall and the outer diameter of the first and second skirts is maximized. The bowl may also include an extension tube connected to the tubular member at the distal end. The extension tube may extend toward the bottom of the plasmapheresis centrifuge bowl such that fluid entering the plasmapheresis centrifuge bowl is introduced nearer to the bottom of the plasmapheresis centrifuge bowl.

BRIEF DESCRIPTION OF THE DRAWINGS

The foregoing features of the invention will be more readily understood by reference to the following detailed description, taken with reference to the accompanying drawings, in which:

FIG. 6 schematically shows a cross section of the neck portion of the plasmapheresis centrifuge bowl shown in FIG. 4, in accordance with some embodiments of the present invention.

FIG. 7 schematically shows a feed tube for use in the plasmapheresis centrifuge bowl shown in FIG. 4, in accordance with various embodiments of the present invention.

FIGS. 12A-12C schematically show various views of a further alternative core, in accordance with some embodiments of the present invention.

DETAILED DESCRIPTION OF SPECIFIC EMBODIMENTS

Illustrative embodiments of the present invention provide plasmapheresis bowls for the separation and collection of plasma. The bowl may have a core and a feed tube that increase the bowl efficiency and reduce foaming within the plasma. Details of the illustrative embodiments are discussed below.

Figure 1:
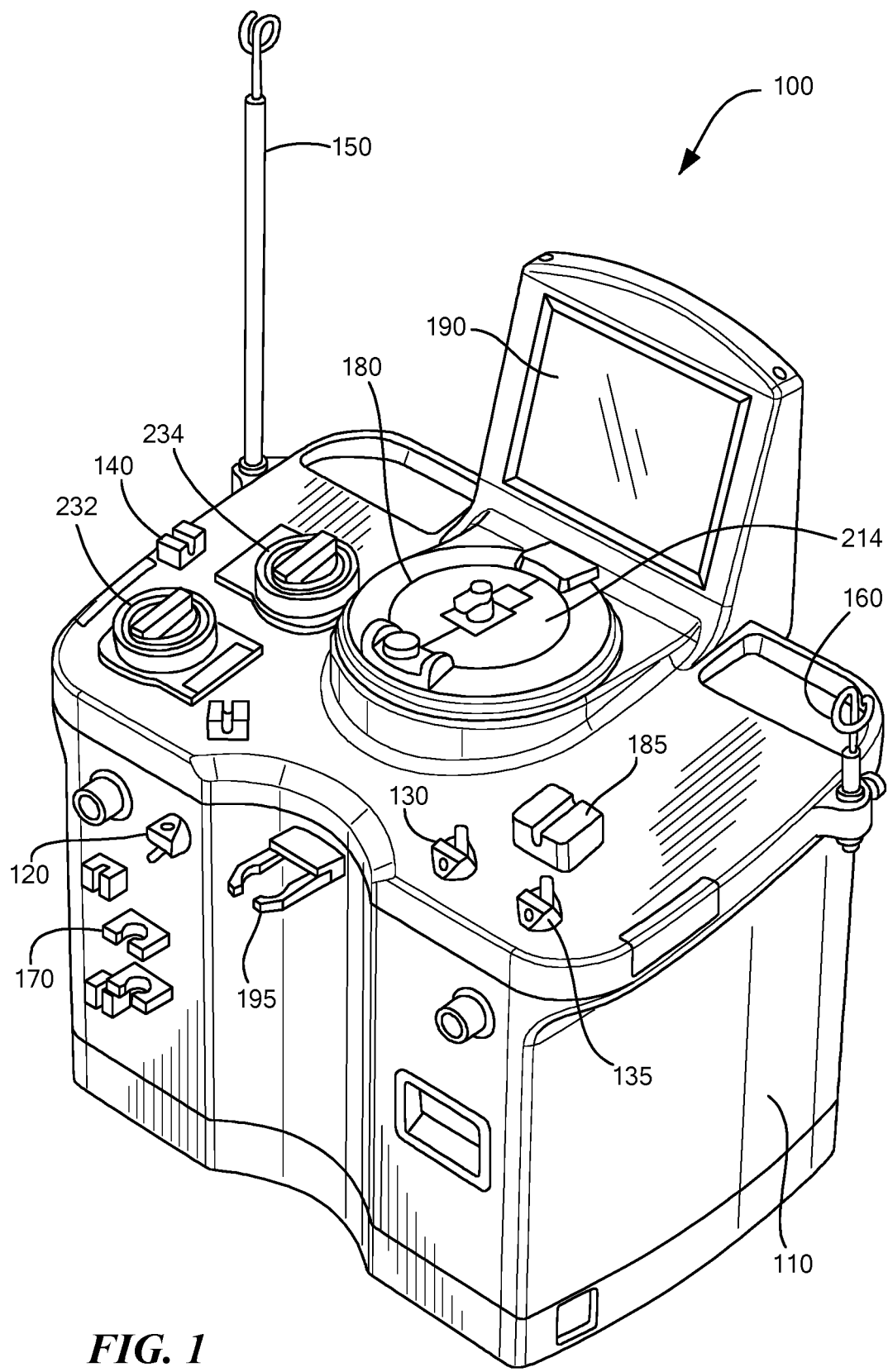
FIG. 1 schematically shows a perspective view of a blood processing system in accordance with some embodiments of the present invention.
Figure 2:
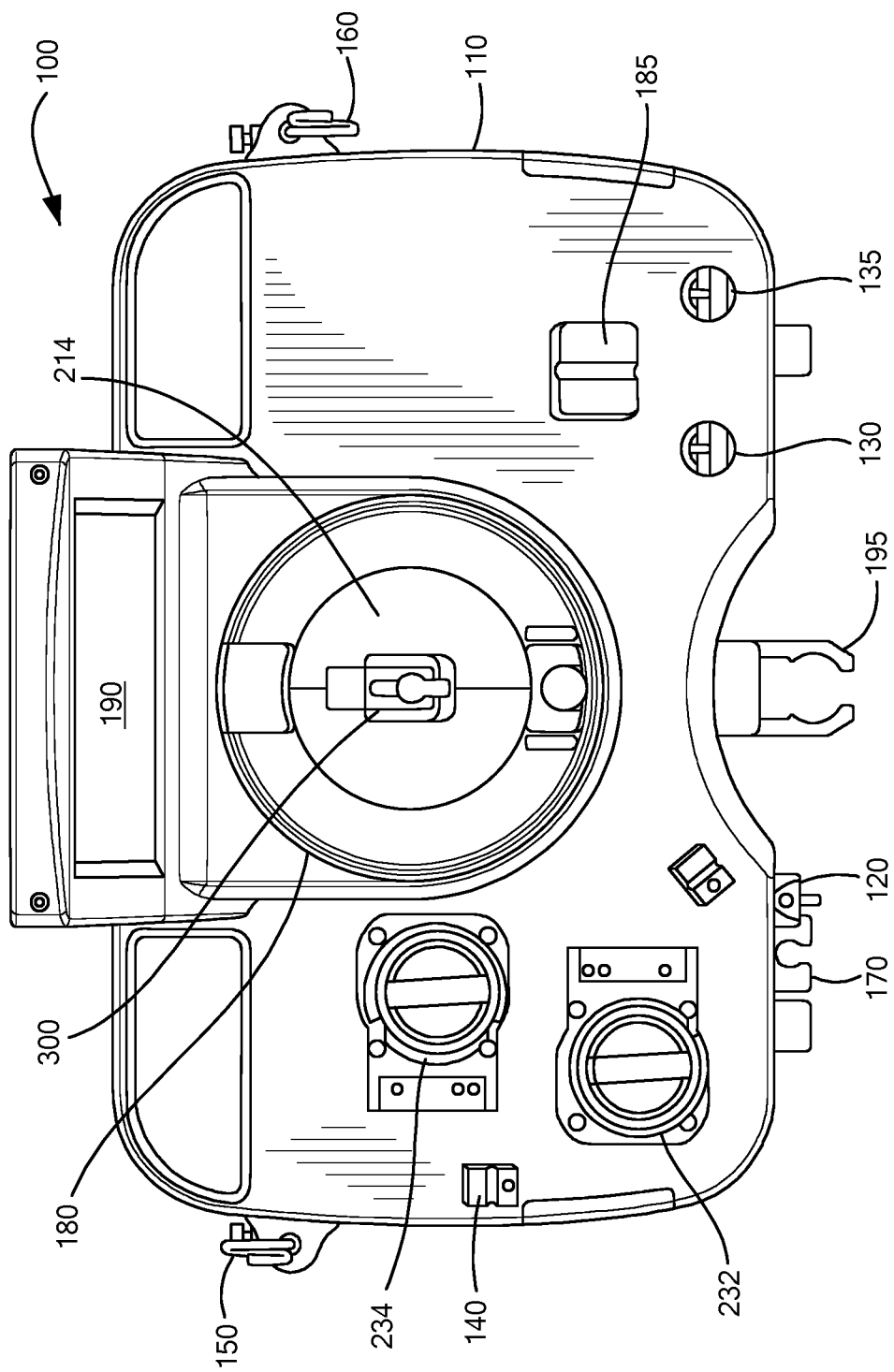
FIG. 2 schematically shows a top view of the blood processing system of FIG. 1, in accordance with some embodiments of the present invention.
Figure 3:
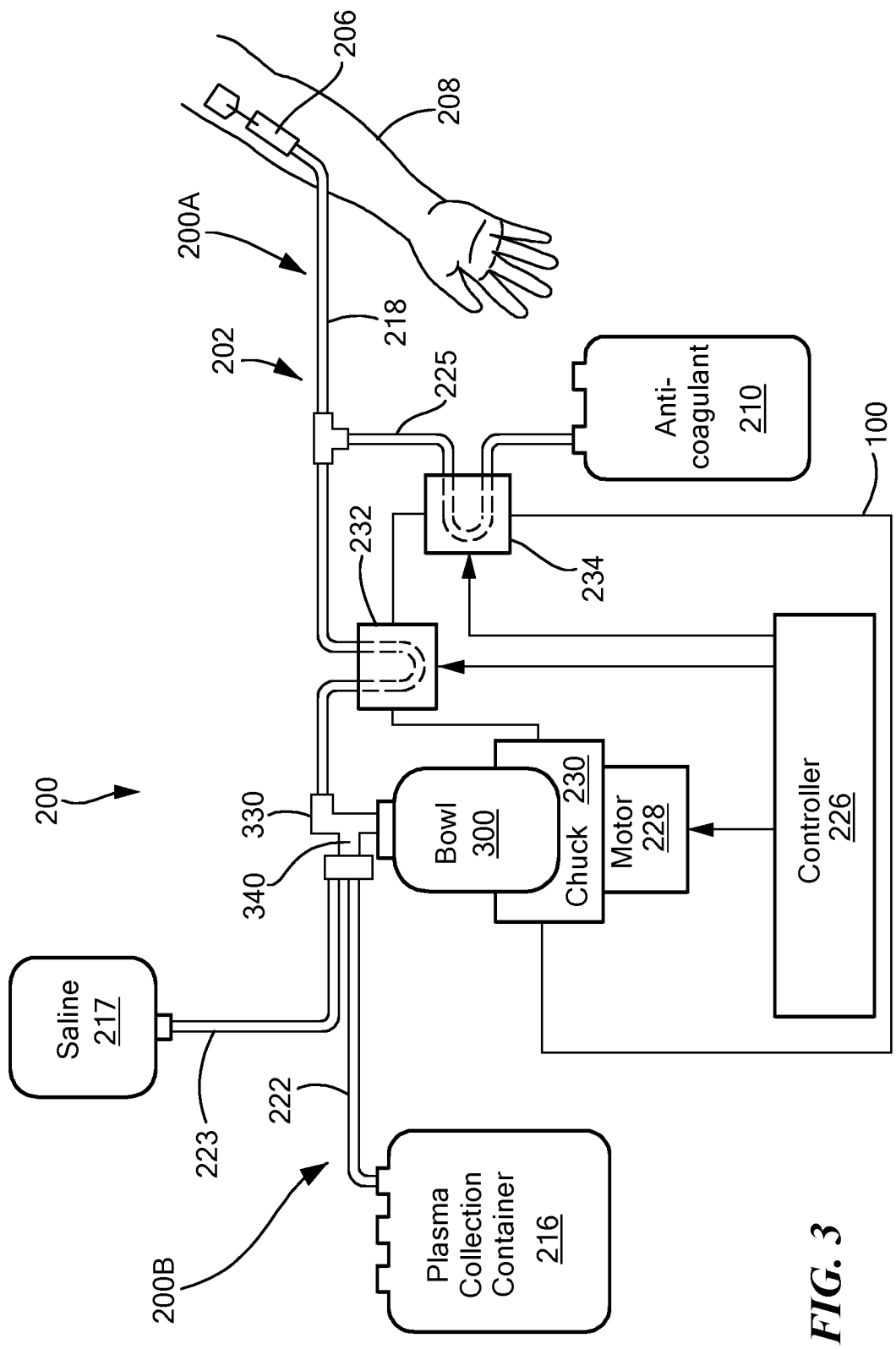
FIG. 3 schematically shows a disposable set installed within a blood processing system, in accordance with some embodiments of the present invention.

As shown in FIGS. 1 and 2, the blood processing system 100 includes a cabinet 110 that houses the main components of the system 100 (e.g., the non-disposable components). Within the cabinet 110, the system 100 may include a first/blood pump 232 that draws whole blood from a subject, and a second/anticoagulant pump 234 that pumps anticoagulant through the system 100 and into the drawn whole blood. Additionally, the system 100 may include a number of valves that may be opened and/or closed to control the fluid flow through the system 100. For example, the system 100 may include a donor valve 120 that may open and close to selectively prevent and allow fluid flow through a donor line 218 (e.g., an inlet line; FIG. 3), and a plasma valve 130 that selectively prevents and allows fluid flow through an outlet/plasma line 222 (FIG. 3). Some embodiments may also include a saline valve 135 that selectively prevents and allows saline to flow through a saline line 223.

To facilitate the connection and installation of a disposable set and to support the corresponding fluid containers, the system 100 may include an anticoagulant pole 150 on which the anticoagulant solution container 210 (FIG. 3) may be hung, and a saline pole 160 on which a saline solution container 217 (FIG. 3) may be hung (e.g., if the procedure being performed requires the use of saline). Additionally, in some applications, it may be necessary and/or desirable to filter the whole blood drawn from the subject for processing. To that end, the system 100 may include blood filter holder 170 in which the blood filter (located on the disposable set) may be placed.

As discussed in greater detail below, apheresis systems 100 in accordance with embodiments of the present invention withdraw whole blood from a subject through a venous access device 206 (FIG. 3) using the blood pump 232. As the system 100 withdraws the whole blood from the subject, the whole blood enters a blood component separation device 214, such as a plasmapheresis centrifuge bowl 300 like that shown in FIG. 4, (a Latham type centrifuge or other type of separation chambers and devices may alternatively be used). The blood component separation device 214 separates the whole blood into its constituent components (e.g., red blood cells, white blood cell, plasma, and platelets). Accordingly, to facilitate operation of the separation device 214, the system 100 may also include a well 180 in which the separation device 214 may be placed and in which the separation device 214 rotates (e.g., to generate the centrifugal forces required to separate the whole blood).

To allow the user/technician to monitor the system operation and control/set the various parameters of the procedure, the system 100 may include a user interface 190 (e.g., a touch screen device) that displays the operation parameters, any alarm messages, and buttons which the user/technician may depress to control the various parameters. Additional components of the blood processing system 100 are discussed in greater detail below (e.g., in relation to the system operation).

FIG. 3 is a schematic block diagram of the blood processing system 100 and a disposable collection set 200 (with an inlet disposable set 200A and an outlet disposable set 200B) that may be loaded onto/into the blood processing system 100, in accordance with the present invention. The collection set 200 includes a venous access device 206 (e.g., a phlebotomy needle) for withdrawing blood from a donor's arm 208, a container of anti-coagulant 210, a centrifugation bowl 300 (e.g., a blood component separation device), a saline container 217, and a final plasma collection bag 216. The blood/inlet line 218 couples the venous access device 206 to an inlet port 330 of the bowl 300, the plasma/outlet line 222 couples an outlet port 340 of the bowl 300 to the plasma collection bag 216, and a saline line 223 connects the outlet port 340 of the bowl 300 to the saline container 217. An anticoagulant line 225 connects the anti-coagulant container 210 to the inlet line 218. In addition to the components mentioned above and as shown in FIG. 3, the blood processing system 100 includes a controller 226, a motor 228, and a centrifuge chuck 230. The controller 226 is operably coupled to the two pumps 232 and 234, and to the motor 228, which, in turn, drives the chuck 230. The controller 226 may be operably coupled to and in communication with the user interface 190.

In operation, the disposable collection set 200 (e.g., the inlet disposable set 200A and the outlet disposable set 200B) may be loaded onto/into the blood processing system 100 prior to blood processing. In particular, the blood/inlet line 218 is routed through the blood/first pump 232 and the anticoagulant line 225 from the anti-coagulant container 210 is routed through the anticoagulant/second pump 234. The centrifugation bowl 300 may then be securely loaded into the chuck 230. Once the bowl 300 is secured in place, the technician may install the outlet disposable set 200B. For example the technician may connect a bowl connector to the outlet 340 of the bowl 300, install the plasma container 216 into the weight senor 195, run the saline line 223 through valve 135, and run the plasma/outlet line 222 through valve 130 and the line sensor 185. Once the disposable set 200 is installed and the anticoagulant and saline containers 210/217 are connected, the system 100 is ready to begin blood processing.

As shown in FIG. 3, the system 100 may also include an optical sensor 213 that may be applied to a shoulder portion of the bowl 300. The optical sensor monitors each layer of the blood components as they gradually and coaxially advance toward the core from the outer wall of the bowl 300. The optical sensor 213 may be mounted in a position (e.g., within the well 180) at which it can detect the buffy coat and/or the red blood cells reaching a particular radius, and, as discussed in greater detail below, the system 100 may alter the plasmapheresis in response to the detection.

Figure 4:
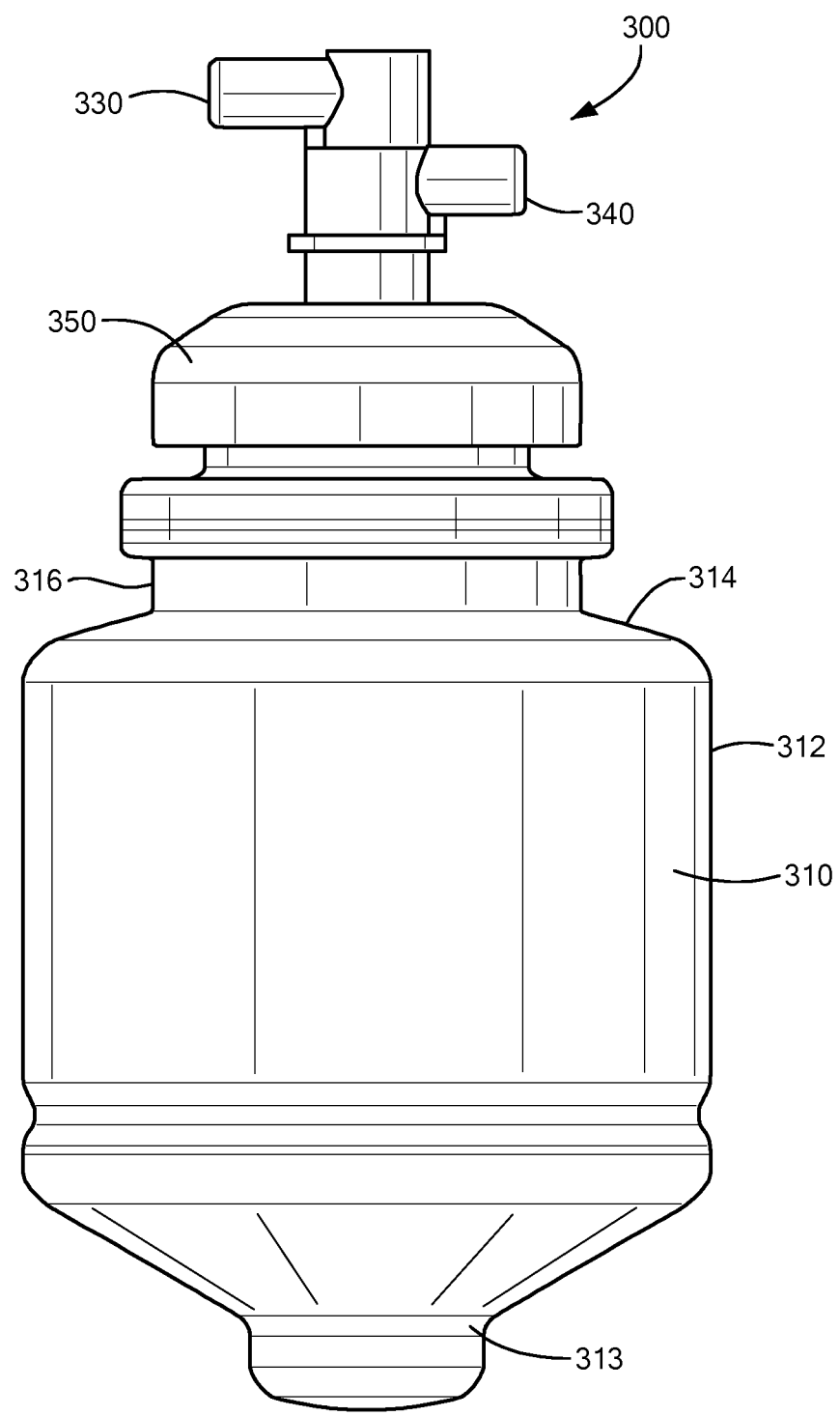
FIG. 4 schematically shows a plasmapheresis centrifuge bowl for use with the system shown in FIGS. 1-3, in accordance with some embodiments of the present invention.
Figure 5:
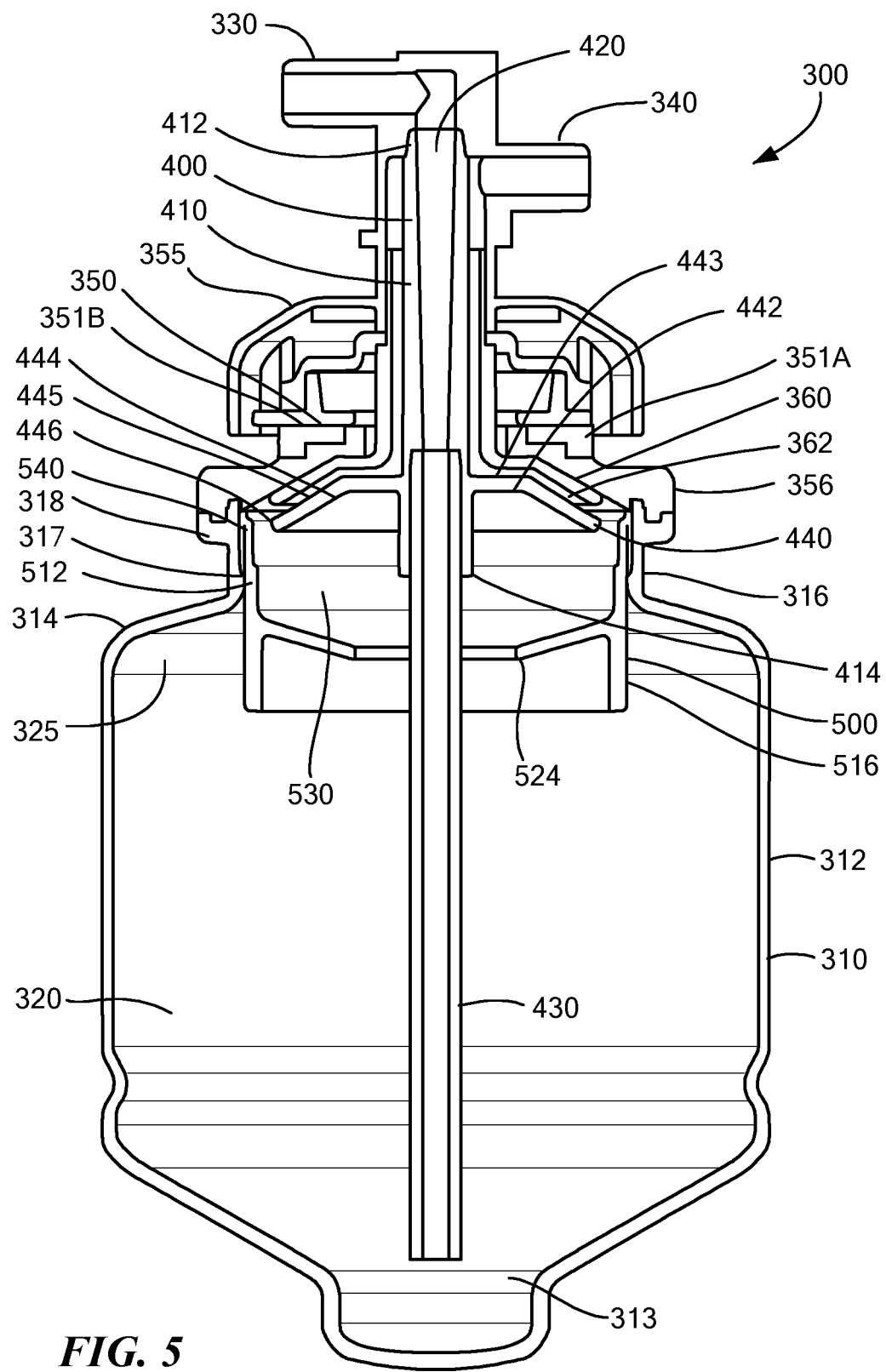
FIG. 5 schematically shows a cross section of the plasmapheresis centrifuge bowl shown in FIG. 4, in accordance with some embodiments of the present invention.

FIGS. 4 and 5 schematically show a perspective view and a cross-sectional view of a centrifuge bowl 300 (e.g., a plasmapheresis bowl) that may be used in conjunction with the system described above. The bowl 300 has an outer body 310 that defines the structure of the bowl 300 and an inner volume 320 into which the whole blood may be introduced for processing. The outer body 310, in turn, includes a main wall 312, a neck portion 316, and shoulder portion 314 that connects the main wall 312 and the neck portion 316. As discussed in greater detail below, the bowl 300 is rotatable about an axis in order to separate the whole blood into its various components (e.g., plasma, red blood cells, etc.).

As discussed above, the bowl 300 may have an inlet 330 that allows whole blood to be introduced into the bowl 300, and outlet port 340 that allows plasma (or other blood component) to be extracted from the bowl 300. To allow the inlet 330 and outlet 340 to remain stationary during bowl rotations, and as best shown in FIGS. 5 and 6, the centrifuge bowl 300 may include a rotary seal 350 that connects the ports (e.g., the inlet 330 and outlet 340) to the outer body 310 of the bowl 300. The rotary seal 350 may include two rings (e.g., a ceramic ring 351A and a carbon ring 351B). One ring (e.g., the ceramic ring 351A) is attached to the seal crown 356 which, in turn, is attached to the outer body 310. The rotary seal 350 allows the bowl 300 (and a core 500 within the interior, discussed in greater detail below) to spin while the inlet 330 and outlet 340 remain stationary.

In some embodiments, it may be beneficial to introduce the whole blood near the bottom of the bowl 300. To that end, the bowl 300 may include a feed tube 400 that extends from the header assembly 355 of the bowl 300 into the interior 320 of the bowl 300. As shown in FIG. 7, the feed tube 400 includes a tubular member 410 with a flow path 420 extending through it to allow the whole blood to flow through the feed tube 400. One end of the tubular member 410 (e.g., the proximal end 412) and the flow path 420 are fluidly connected to the inlet port 330. At the distal end 414 of the tubular member 410, the feed tube 400 has an extension tube 430 that extends from the tubular member 410, through the core 500 (discussed in greater detail below) and toward the bottom of the bowl 300 (e.g., so that liquid flowing through the feed tube 400 is discharged at the base 313 of the bowl body 310).

Nearer the distal end 414 of the tubular member 410, the feed tube 400 has a skirt 440 that extends radially outward from the tubular member 410. For example, the skirt 440 has a first portion 442 that extends generally perpendicularly out from the tubular member 410 such that one or more of the surfaces of the first portion 442 (e.g., the top surface 443) is perpendicular to the longitudinal axis of the tubular member 410. Extending from the first portion 442, the skirt 440 may have an angled portion 444 that extends both radially outward from the first portion 442, and downward/distally such that the top surface 445 of the angled portion 444 is angled downward (e.g., it is not perpendicular to the longitudinal axis of the tubular member 410). It should be noted that the angled portion 444 may have a constant angle along the length or the angle may change gradually or in a step-wise fashion along the length of the angled portion 444.

The skirt 440 and a second skirt/disk 360 on the header assembly 355 of the bowl 300 may form an effluent channel 362 that is fluidly connected to the outlet 340 to allow blood components within the collection chamber 530 (discussed in greater detail below) to exit the bowl 300. To create this effluent channel 362, the skirt 440 may have a number (e.g., three) of spacing ribs 460 that maintain separation between the skirt 440 on the feed tube 400 and the skirt 360 on the header assembly 355 (e.g. to allow fluid to flow between the skirts 440/360). The spacing ribs 460 may be located just on the top surface 443 of the first portion 442 or, as shown in FIG. 7, the spacing ribs 460 may extend along the top surface 443 and up the outer surface of the tubular member 410. It should be noted that, although FIG. 7 shows three spacing ribs 460 that are equally spaced about the tubular member 410 and top surface 443, other embodiments may have more or less than three spacing ribs 460. Additionally or alternatively, the spacing ribs 460 may not be equally spaced about the tubular member 410 and top surface 443 (e.g., they may be irregularly spaced).

As noted above, the header assembly 355 of the bowl 300 (including the inlet 330 and outlet 340) does not rotate with the bowl 300. Accordingly, because the feed tube 400 is connected to the header assembly 355, it similarly does not rotate with the bowl 300. Therefore, during collection of plasma via the effluent channel 362, the stationary skirts 360/440 (e.g., creating the effluent channel) can impart a shear force on the spinning plasma component which, in turn, can cause foaming. However, by utilizing a smooth angled portion 444/angled surface 445, various embodiments of the present invention are able to reduce the shear force and, in turn, reduce foaming within the plasma. It should be noted that, because the spacing ribs 460 are located further down the effluent channel 362 and the rotation speed of the fluid/plasma has dropped by the time it reaches the ribs 460, the spacing ribs 460 do not impart significant shear force/turbulence. Additionally or alternatively, in some embodiments, the end 446 of the angled portion 444 (e.g., the outermost portion of the skirt 440) may be rounded, chamfered or have other configurations that help reduce the shear force and/or help fluid enter the effluent channel 362.

As noted above, various embodiments of the present invention include a core 500 located within the interior of the bowl 300. As shown in FIGS. 8A-8E, the core 500 may include a cylindrical body 510 that defines the overall structure of the core 500. Within the interior of the cylindrical body 510, the core 500 includes a ledge 520 that extends radially inward from the inner surface of the cylindrical body 510. The portion of the cylindrical body 510 located above the ledge 520 (e.g., the proximal portion 512) and the ledge 520 form a collection chamber 530 within the interior of the core 500 and in which the effluent channel 362 (formed by the skirts 360/440) is located (e.g., so that the plasma may be extracted from the collection chamber 530. To that end, the inner surface 514 of the proximal portion 512 (e.g., the wall formed by the proximal portion 512) establishes the exterior boundary of the collection chamber 530. The ledge 520 (e.g., the top surface 522 of the ledge 520) establishes the lower boundary of the collection chamber 530 and creates a surface for incoming plasma to establish itself upon. The ledge 520 (e.g., the bottom surface 526 of the ledge 520) also prevents fluid within the bowl 300 and below the core 500 from entering the collection chamber 530.

In addition to defining the collection chamber 530, the proximal portion 512 of the core 500 also helps to isolate the collection chamber 530 from the separation chamber 325 within the bowl 300 (e.g., because fluid from the separation chamber 325 must flow up and over the wall of the proximal portion 512 to reach the collection chamber 530). By isolating the collection chamber 530 from the separation chamber 325, the proximal portion 512 prevents disrupting forces (e.g., shear forces, turbulent forces, etc.) created by the spinning fluid in the collection chamber 530 (e.g., plasma) contacting the stationary skirts 360/440 from entering the separation chamber 325. By preventing these forces from reaching the separation chamber 325, various embodiments of the present invention are able to maintain tighter packed cell layers (which would otherwise be disrupted by the turbulence that reaches the separation chamber 325). This, in turn, increases collection efficiency and ensures that the signals from the optical sensor 213 are cleaner and more consistent (discussed in greater detail below).

In addition improving the optical sensor 213 signals and allowing the cell layers to remain more tightly packed, the wall (e.g., the proximal portion 512) also helps to reduce foaming within the plasma in several ways. For example, because the proximal portion 512 isolates the collection chamber 530 and the separation chamber 325, the fluid (e.g., plasma) stays within the collection chamber 530 when the flow rates within the system 100 decrease or stop (e.g., due to whole blood pump 232 regulation by the system 100). This, in turn, keeps the collection chamber 530 filled to a level where the skirts 360/440 (and the effluent channel 362) remain wetted, and prevents air from mixing with the plasma. Additionally, the proximal portion 512 helps to form a stable fluid layer (comprised of the first volume of plasma entering the collection chamber 530) on the inside wall of the proximal portion 512 in the collection chamber 530. This stable fluid layer helps to stabilize the new/incoming fluid by residing below the entry point of the collection skirt 360/440, and allowing the new plasma to "ride" on top and quickly exit through the collection skirt (e.g., the effluent channel 362). This minimizes the mixing of the new/incoming fluid with air, reduces foam generation, and improves the line sensor 185 signal (which allows the system 100 to more accurately detect changes in cellular content exiting the bowl 300 and improves system efficiency).

It should be noted that the location of the ledge 520 may impact the amount of foam generation in the bowl 300. For example, if the ledge 520 is placed too high in the core 500, the spinning core 500 will be located closer to the non-moving skirts 360/440. This, in turn, would result in increased shear forces and foam generation. Additionally, if the ledge 520 is located too low, the plasma entering the collection chamber 530 would have a larger drop to the ledge 520 which can cause the plasma to "crash down" harder on the ledge 520 and increase turbulence and foam generation in the collection chamber 530. Therefore, it is important that that ledge 520 is located far enough from the non-moving skirts 360/440 to minimize the shear forces and turbulence created between the ledge 520 and non-moving skirts 360/440, but not so far that the plasma "crashes down" on the ledge 520. A ledge 520 that is placed lower than the fluid fill level of a full non-spinning bowl 300 may allow the surfaces of the collection chamber 530 to become submerged in red cells during the beginning of return, and after the bowl 300 has fully drained there could still be residual red cells left on the interior surfaces of the core (e.g., on the surface of the proximal wall 512 and on the top surface 522 of the ledge 520) that could be picked up by the plasma of the subsequent cycle when it enters the collection chamber 530.

The proximal portion 512 (e.g., the wall) also helps to prevent red blood cells within the separation chamber 325 from entering the collection chamber 530 when the draw cycle is complete (e.g. when the whole blood pump 232 stops and the centrifuge (e.g., the motor 228 and chuck 230 slow down). As the bowl 300 slows down, there is a decreasing centrifugal force on the blood components of the bowl 300, and as such the separation of blood into cellular layers will be lost. Thus, red cells and other cells that were previously being packed to the outside of the bowl body 310 may mix in with the plasma still within the separation chamber 325. The proximal portion 512 of the core wall may contain this mixing of cellular components with the plasma to the separation chamber 325, and may reduce the entrance of cells from the separation chamber 325 into the collection chamber 530. This allows the plasma within the collection chamber 530 to remain separate from the red blood cells (and other components) even as the bowl 300 slows down. When the bowl 300 is fully drained, there are potentially less red blood cells and other components left as a residue on the interior portion of the core (e.g., on the proximal wall 512 and top surface 522 of the ledge 520), resulting in less cells being picked up by the entering plasma of the subsequent cycle. Therefore, the amount of red blood cells inadvertently collected during plasmapheresis (e.g., between cycles) is greatly reduced.

The portion of the cylindrical body 510 located below the ledge 520 (e.g., the portion 516) provides a reflective surface for the optical sensor 213. In other words, during processing, the optical sensor 213 on the bowl will shine a light into the bowl and the amount of transmission/reflection back to the sensor 213 provides an indication of material layer locations within the bowl 300. The portion 516 of the core 500 below the ledge 520 provides the surface which the light reflects off of and back toward the sensor 213.

In some embodiments, the core 500 may have a constant diameter along its length (e.g., with the exception of the ribs 540, the core 500 may have a smooth/vertical outer surface 513) to ensure that there are no overhangs in which the plasma may be trapped (e.g., because fluid will fill to the diameter of the skirt and is unable flow against the centrifugal force created by the spinning bowl 300). Additionally, if the diameter of any overhang is smaller than the skirts 360/440, the overhang may also cause air to be trapped. This causes a disruption of the optics signal, if the trapped air is in the path of reflectance.

Figure 8A:
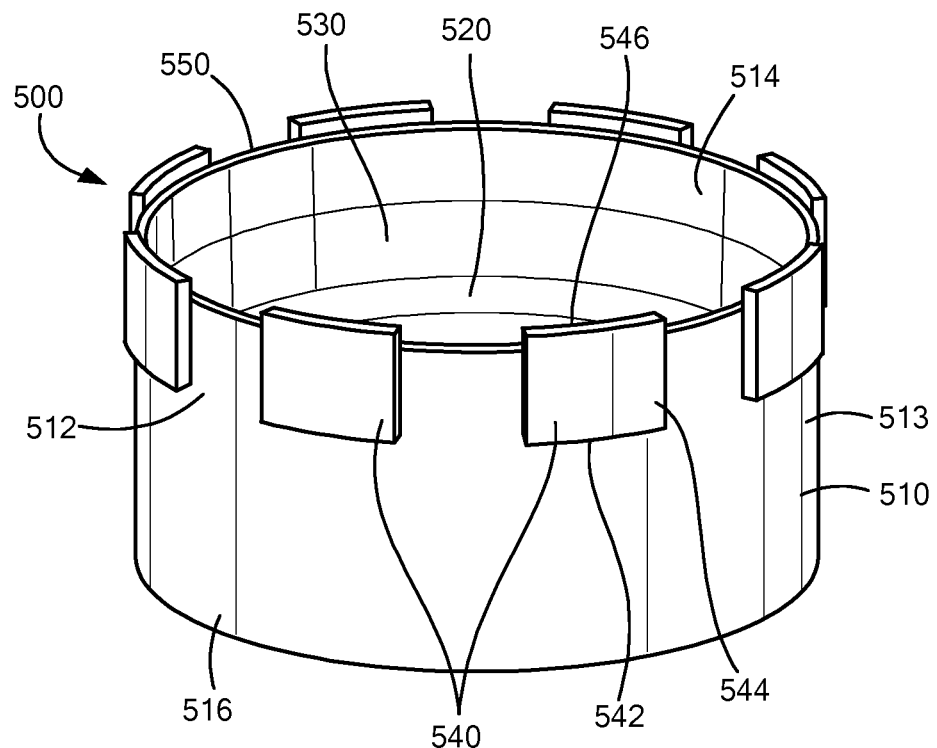
FIGS. 8A-8E schematically show various views of a core for use in the plasmapheresis centrifuge bowl shown in FIG. 4, in accordance with various embodiments of the present invention.
Figure 8B:
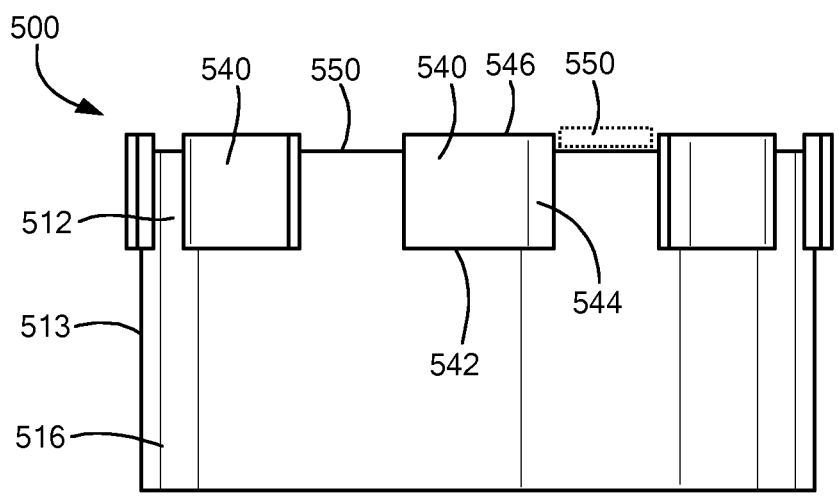
Figure 8C:
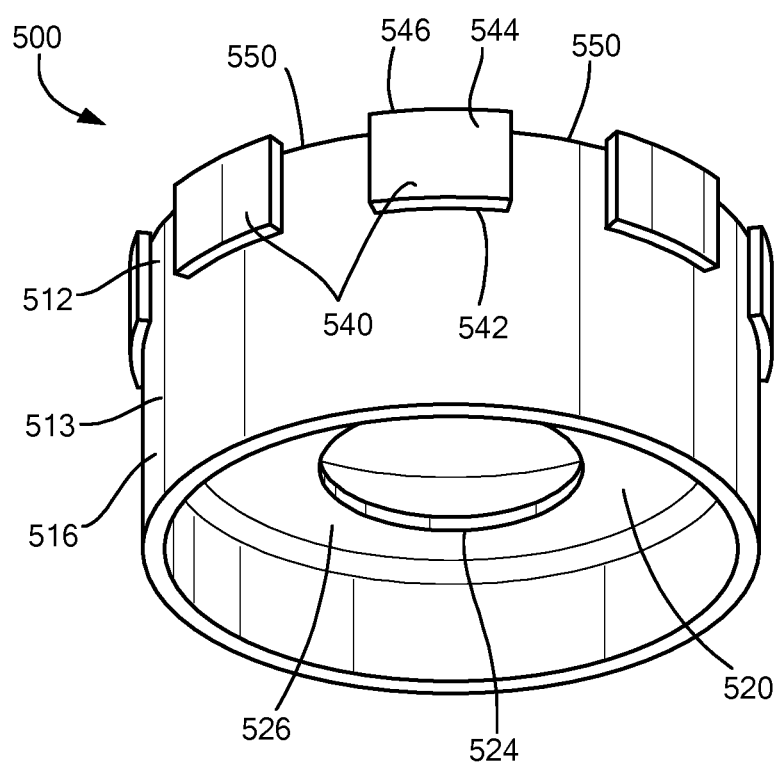
Figure 8D:
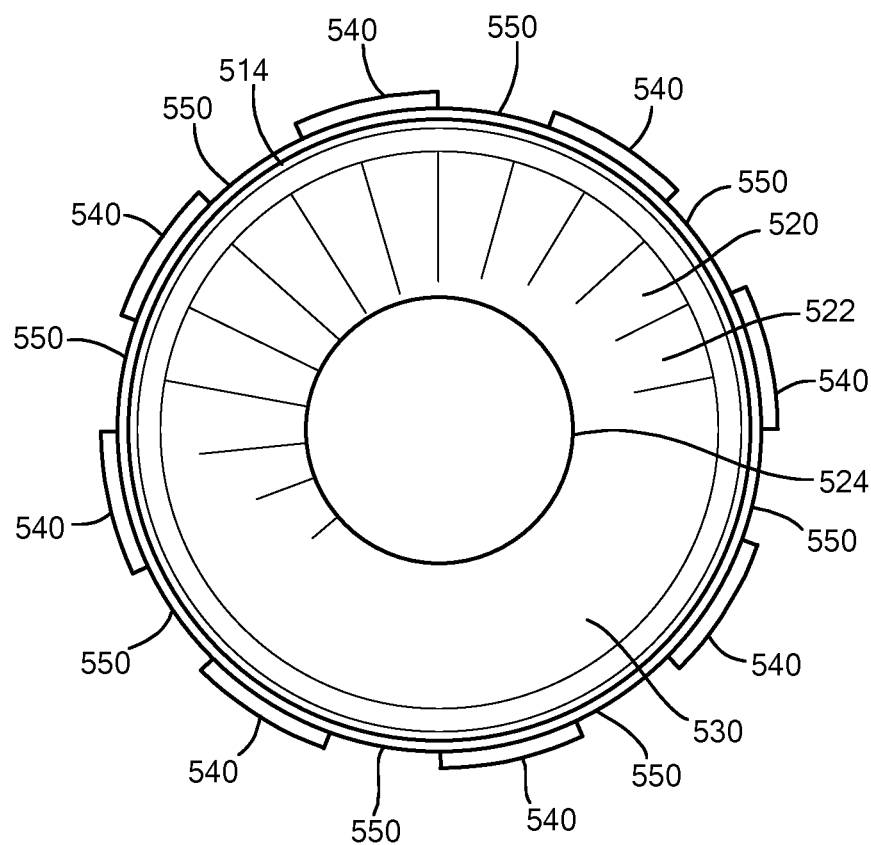
Figure 8E:
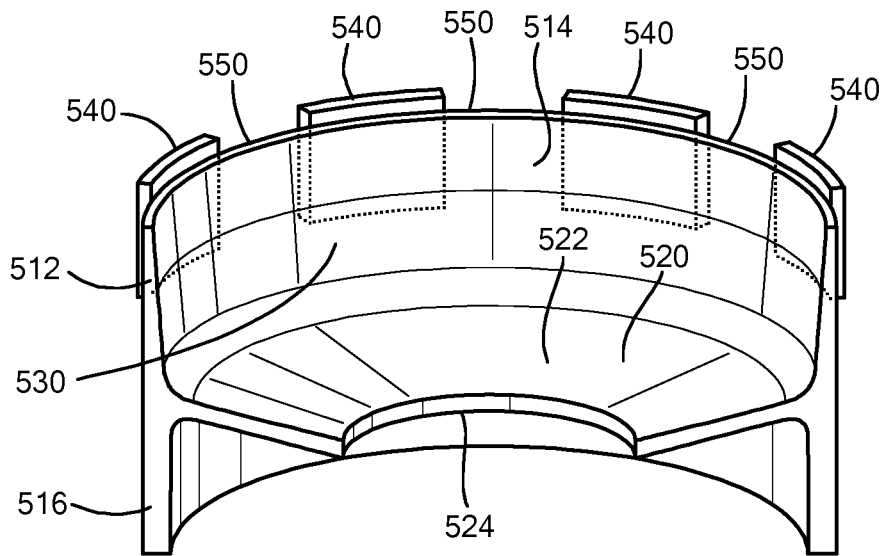

As best shown in FIGS. 8C-8E, the ledge 520 may have an opening 524 (e.g., a hole) extending through the center of it. This opening 524 allows the extension tube 430 of the feed tube 400 to pass through the core 500 and the ledge 520 and provides an opening through which fluid remaining within the collection chamber 530 at the end of processing and plasma collection may exit the collection chamber 530 and drain to the bottom of the bowl 300, for example, so it can be returned to the patient or sent to a separate collection container. To help with the drainage and minimize fluid hold up in the collection chamber 530, the ledge 520 may extend distally (e.g., downward) toward the bottom of the core 500 such that the top surface 522 slopes toward the opening 524

To position and secure the core 500 within the interior of the bowl 300, the core 500 may have a number of ribs 540 near the proximal end (e.g., the top) of the core 500. For example, the bottom surface 542 of the ribs 540 may interface with a mating ledge 317 (FIGS. 5 and 6) on the bowl body 310, and the outer surface 544 of the ribs 540 may interface with the interior face 318 of the neck portion 316 of the bowl 300/bowl body 310. In some embodiments, the interface between the outer surface 544 of the ribs 540 and the interior face 318 of the neck portion 316 may create an interference fit between the bowl 300/bowl body 310 and core 500. To further hold the core 500 in place within the bowl 300 and maintain the vertical location of the core 500 within the bowl 300, the top surface 546 of the ribs 540 may also interface with a seal crown 356 on the header assembly 355.

The ribs 540 may extend proximally (upwards) past the proximal end (e.g., top) of the cylindrical body 510 of the core and may be spaced around the diameter of the cylindrical body 510. In this matter, the ribs 540 create flow channels 550 between them that allow fluid to flow over the proximal portion 512, between the ribs 540 and into the collection chamber 530. It should be noted that, although FIGS. 8A-8E shows eight ribs 540 that are equally spaced about the core 500, other embodiments may have more or less than eight ribs 540. Additionally or alternatively, the ribs 540 may not be equally spaced about the core 500 (e.g., they may be irregularly spaced).

It should also be noted that the sizing and positioning of the core 500 within the bowl 300 may impact the amount of shear force created between the core 500 (which spins during processing) and the skirts 360/440 (which are stationary). Therefore, to minimize the amount of shear forces created (and, as a result, the amount of foam within the plasma), various embodiments of the present invention may maximize the distance between the inner surface 514 of the core 500 and the skirts 360/440. This may be accomplished in several ways. For example, in some embodiments, the thickness of the wall of the bowl 300 may be reduced in the neck portion 316 (e.g., by increasing the inner diameter of the neck portion 316). This allows the core 500 to be wider and, therefore, the distance between the core 500 and skirts 360/440 to be increased. Additionally, by increasing the distance in this manner, other aspects of the bowl 300 (e.g., the overall exterior shape and dimensions of the bowl 300, the location of the bowl body weld, the location of the optics signal transmission, etc.) may remain the same, and the bowl 300 may still be used with existing plasmapheresis systems.

During use and after lines 222/223 are connected and the bowl 300 is installed into the system 100, the user/technician may insert the venous access device 206 into the donor's arm 208 and the controller 226 may activate the two pumps 232, 234 and the motor 228. Operation of the two pumps 232, 234 causes whole blood to be drawn from the donor, anticoagulant from container 210 to be introduced into the drawn whole blood, and the now anticoagulated whole blood to be delivered to the inlet port 330 of the bowl 300.

It should be noted that the anticoagulant line 225 may also include a bacteria filter (not shown) that prevents any bacteria in the anticoagulant source 210, the anticoagulant, or the anticoagulant line 225 from entering the system 100 and/or the subject. Additionally, the anticoagulant line 225 may include an air detector 140 that detects the presence of air within the anticoagulant. The presence of air bubbles within any of the system 100 lines can be problematic for the operation the system 100 and may also be harmful to the subject if the air bubbles enter the blood stream. Therefore, the air detector may be connected to an interlock that stops the flow within the anticoagulant line 225 in the event that an air bubble is detected (e.g., by stopping the anticoagulant pump 234), thereby preventing the air bubbles from entering the subject.

As the anti-coagulated whole blood is withdrawn from the subject and introduced into the plasmapheresis bowl 300. The whole blood will flow through the feed tube 400 and extension tube 430 and into the bowl 300 near the bottom 313 of the bowl 300. The centrifugal forces caused by the bowl rotation will cause the whole blood to move toward the outer wall 312 of the bowl 300, and the blood component separation device 214 (e.g., the bowl 300) will separate the whole blood into several blood components. For example, the bowl 300 may separate the whole blood into a first, second, third, and, perhaps, fourth blood component. More specifically, the bowl 300 (and the centrifugal forces created by rotation of the bowl 300) can separate the whole blood into plasma, platelets, red blood cells ("RBC"), and, perhaps, white blood cells ("WBC"). The higher density component, i.e., RBC 580, is forced to the outer wall of the bowl 300 while the lower density plasma 590 lies nearer the core 500. A buffy coat 585 is formed between the plasma and the RBC. The buffy coat 585 is made up of an inner layer of platelets, a transitional layer of platelets and WBC and an outer layer of WBC.

As shown in FIG. 3 and as briefly discussed above, the system 100 may also include an optical sensor 213 that may be applied to a shoulder portion 314 of the bowl 300. The optical sensor 213 monitors each layer of the blood components as they gradually and coaxially advance toward the core from the outer wall of the bowl 300. The optical sensor 213 may be mounted in a position (e.g., within the well 180) at which it can detect the buffy coat and/or the red blood cells reaching a particular radius, and the steps of drawing the whole blood from the subject/donor and introducing the whole blood into the bowl 300 may be altered and/or terminated in response to the detection.

Figure 9A:
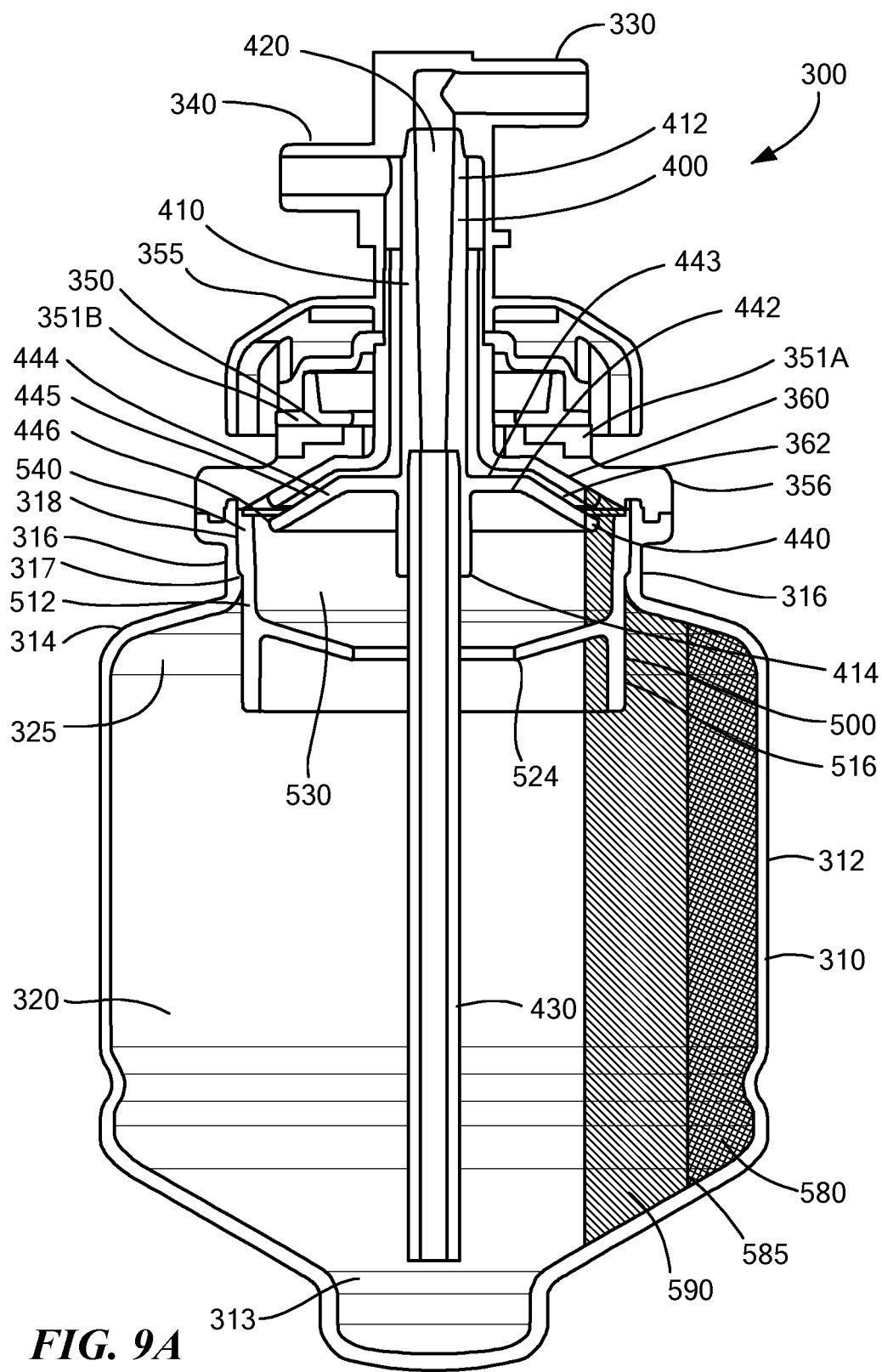
FIGS. 9A-9B schematically show the plasmapheresis centrifuge bowl shown in FIG. 4 during blood processing, in accordance with various embodiments of the present invention.
Figure 9B:
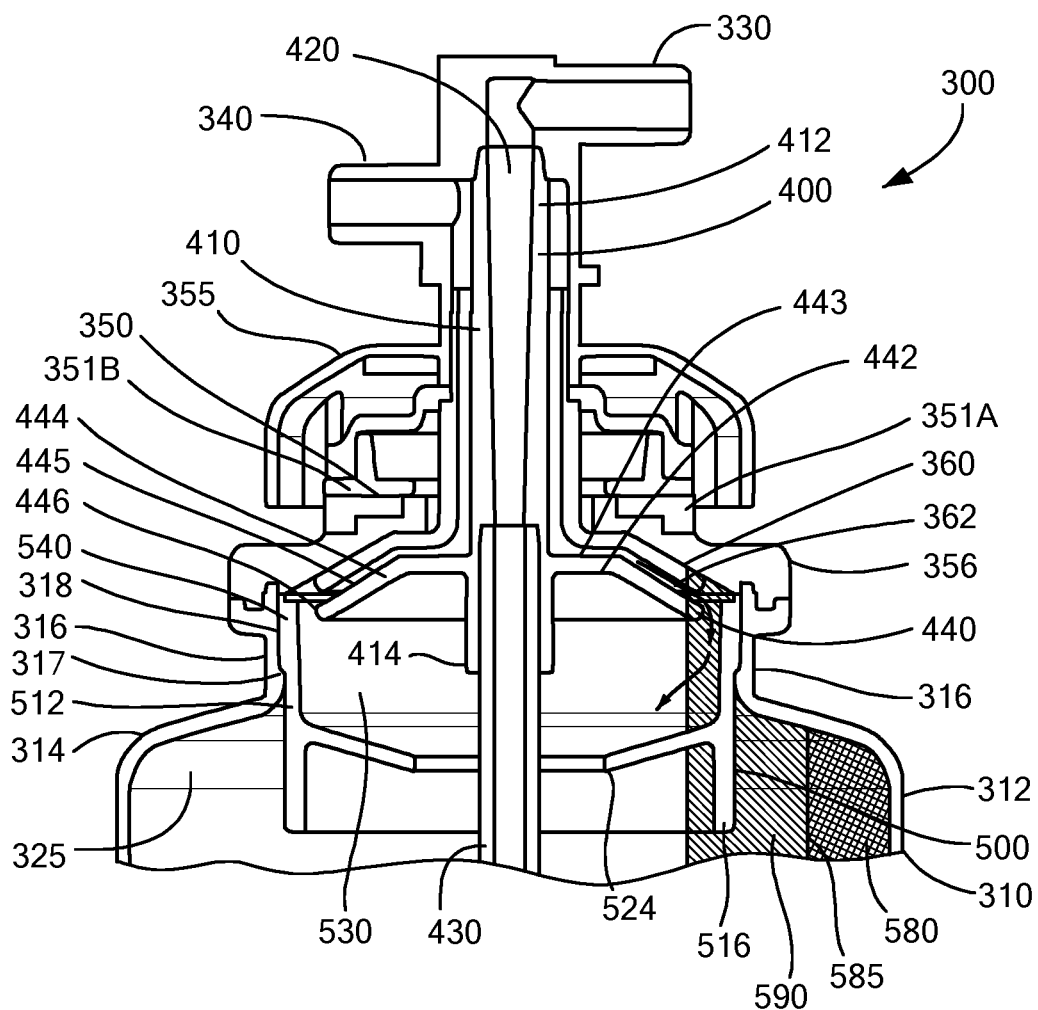

Once the bowl 300 has separated the blood into the various components (e.g., red blood cells 580 and plasma 590, FIGS. 9A and 9B), one or more of the components can be removed from the bowl 300. For instance, as additional anticoagulated whole blood enters the bowl 300, the plasma 590 will be forced further inward toward the core 500 until it flows over the proximal portion 512 of the core 500 and into the collection chamber 530. When the collection chamber 530 fills with plasma such that the plasma within the collection chamber 530 makes sufficient contact with the skirts 360/440 and effluent channel 362 (FIGS. 9A and 9B), the plasma will begin exiting the bowl 300 via the effluent channel 362 and the outlet 340. Once out of the bowl 300, the plasma will flow through line 222 and into the plasma collection container 216. Some embodiments of the system 100 may include a weight sensor 195 (FIG. 1) that measures the amount of plasma collected. The plasma collection process may continue until a target or pre-determined volume of plasma is collected within the plasma collection container 216.

As noted above, in some embodiments, the system 100 may also include a line sensor 185 that can determine the type of fluid (e.g., plasma, platelets, red blood cells etc.) exiting the bowl 300. In particular, the line sensor 185 consists of an LED which emits light through the blood components leaving the bowl 300 and a photo detector which receives the light after it passes through the components. The amount of light received by the photo detector is correlated to the density of the fluid passing through the line. For example, if plasma is exiting the bowl 300, the line sensor 185 will be able to detect when the plasma exiting the bowl 300 becomes cloudy with platelets (e.g., the fluid existing the bowl 300 is changing from plasma to platelets). The system 100 may then use this information to either stop the removal of blood components from the bowl 300, stop drawing whole blood from the subject, or redirect the flow by, for example, closing one valve an opening another.

Once the system 100 has collected the target volume of plasma within the plasma collection container 216 or the bowl 300 is full of red blood cells, the system 100 can return the remaining components (e.g., the components remaining within the bowl 300) to the subject. For example, when all the plasma has been removed and the bowl 300 is full of RBCs (and any other blood component not collected), the controller 226 stops the draw of whole blood from the subject and slows and/or stops the bowl 300. As the bowl 300 slows and/or stops, and fluid remaining within the collection chamber 530 will drain out of the collection chamber 530 via the opening 524 in the ledge 520. The system 100/controller 226 may then reverse the direction of the blood/first pump 232 to draw the RBCs (and other components) from the bowl 300 and send them back to the subject. Alternatively, if the system 100 is so equipped, the system 100 may return the components to the subject via a dedicated return line.

In addition to the non-collected blood components (e.g., the components remaining in the bowl 300), the system 100 may also return saline to the patient/subject. The saline may be used as a compensation fluid to make up for the volume of the blood component (e.g., plasma) that was removed and collected, and is not being returned to the patient. To that end, during the return step, the saline valve 135 may be opened to allow saline from the saline container 217 to flow through the saline line 223 and into the bowl 300 (via outlet 340), where it can be returned to the patient/donor with or after the remaining blood components. If additional plasma collection cycles are to be performed (e.g., if the volume of plasma already collected does not equal the target/pre-determined volume), the system 100 may once again start the blood/first pump 232 to withdraw whole blood from the subject and the system 100 may repeat the process above until the target volume of plasma is collected.

Figure 10:
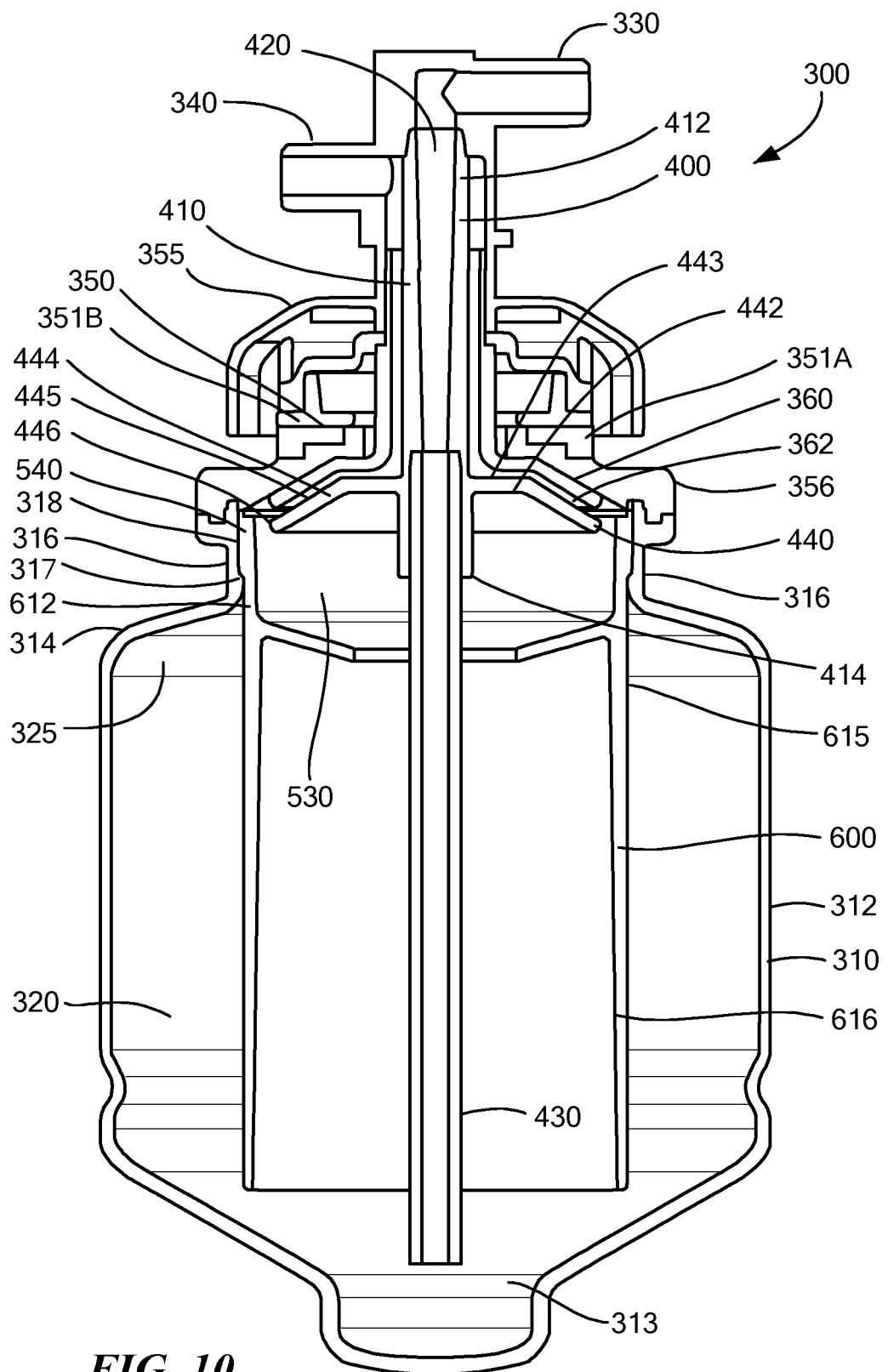
FIG. 10 schematically shows a cross-sectional view of a plasmapheresis centrifuge bowl with an alternative core, in accordance with alternative embodiments of the present invention.
Figure 11A:
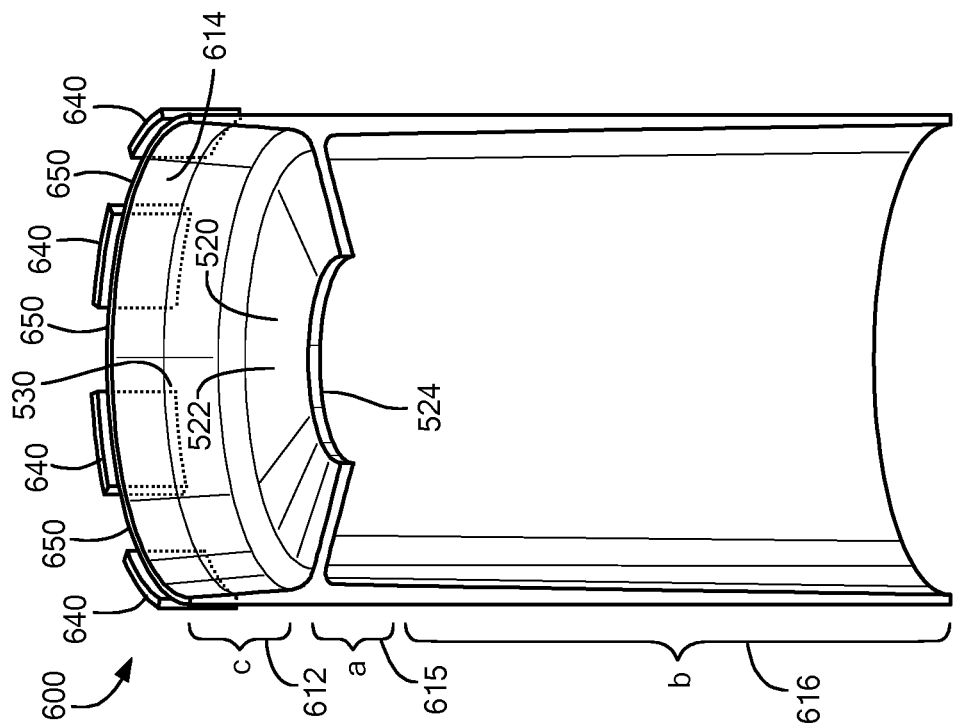
FIGS. 11A-11B schematically show various views of the alternative core shown in FIG. 10, in accordance with some embodiments of the present invention.
Figure 11B:
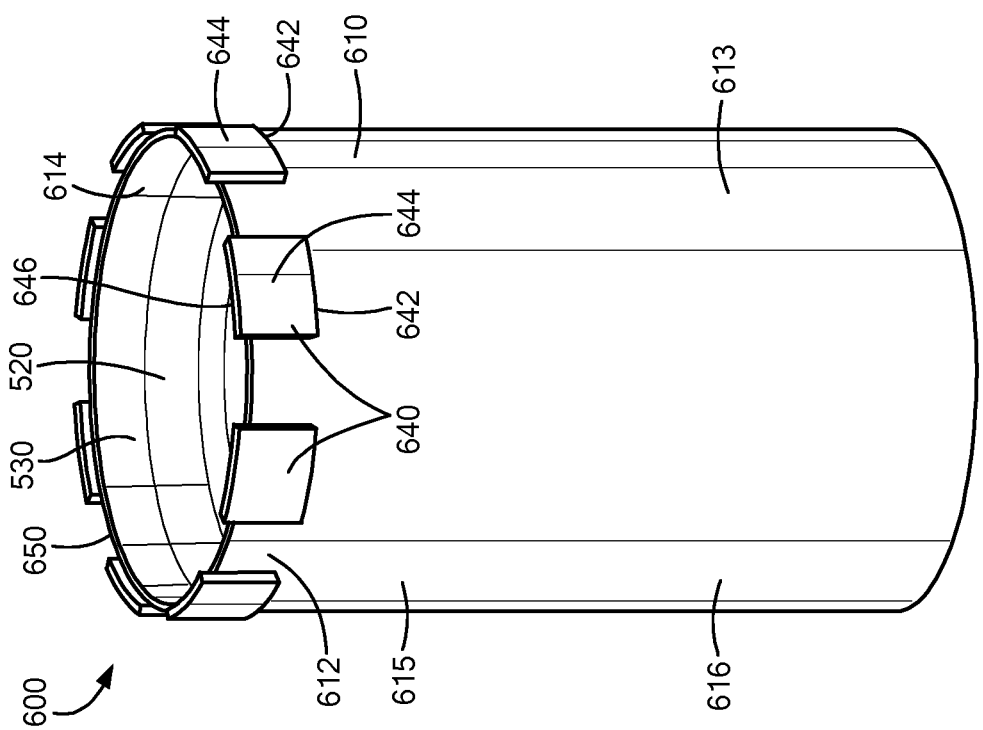

FIG. 10 schematically shows a plasmapheresis bowl 300 with an alternative embodiment of the core (e.g., a "long" core 600). FIGS. 11A and 11B schematically show a perspective view and a cross-sectional view of the alternative core 600. As can be seen in FIGS. 11A and 11B, the "long" core 600, like the core 500 shown in FIGS. 8A-8E, has a cylindrical body 610 that defines the overall structure of the core 600, and a ledge 520 that extends radially inward from the inner surface of the cylindrical body 610. Also like the core 500 shown in FIGS. 8A-8E, the proximal portion 612 of the body 610 (e.g., the inner surface 614 of the proximal portion 612) located above the ledge 520 and the ledge 520 form the collection chamber 530. The core 600 also has a number of ribs 640 that position and secure the core 600 within the bowl 300 in a similar manner as that described above. For example, the bottom surface 642 of the ribs 640 may interface with the mating ledge 317 (FIG. 10) on the bowl body 310, the outer surface 644 of the ribs 640 may interface with the interior face 318 of the neck portion 316 of the bowl 300, and the top surface 646 of the ribs 640 may interface with the seal crown 356 on the header assembly 355 (e.g., to maintain the vertical location within the bowl 300). The spaces between the ribs 640 also create flow channels 650 that allow fluid to flow between the ribs 640 and into the collection chamber 530.

Unlike the core 500 shown in FIGS. 8A-8E, the portion of the long core 600 embodiment below the ledge 520 is significantly longer and extends further downward into the bowl 300. For example, directly under the ledge 520, the core 600 may include an intermediate portion 615 that performs a function similar to that described above for the portion 516 of the core 500 shown in FIGS. 8A-8E. In particular, the intermediate portion 615 may provide reflective surface for the optical sensor 213. Directly below the intermediate portion 615, the core 600 may have an extended distal portion 616 that extends further downward into the bowl 300.

In some instances, this long core 600 can provide some benefits over the shorter version of the core. In particular, during processing, fluid may become trapped in the space under the collection chamber 530 and ledge 520 and inside of the wall of portion 516. However, by extending further into the bowl 300 and taking up more volume within the interior of the bowl 300, the extended distal portion 616 of the long core 600 helps to prevent some of the fluid/plasma from becoming trapped, which allows more plasma to exit the bowl and increases the collection efficiency. Although the extended distal portion 616 is shown as a relatively thin wall, other embodiments may have a thick walled extended distal portion 616 (under the collection chamber 530) to take up more volume under the collection chamber 530, which may prevent even more fluid/plasma from being trapped. Alternatively, the core 600 may have a second ledge (not shown) extending radially inward from the bottom of the extended/distal portion 616 to prevent fluid from traveling inside of the distal portion of the core 600.

The extended distal portion 616 of the long core 600 also helps to stabilize the plasma layer within the separation chamber 325. For example, as noted above, as the whole blood separates into its various components, the plasma is located nearest to the center of the bowl 300 (e.g., nearest the core 500/600). The extended distal portion 616 of the long core 600 provides a solid contact surface for the plasma (which is spinning at the same rate as the core 600), as opposed to the air cylinder (e.g., the area radially inward from the plasma layer that is taken up by air rather than a blood component). By providing the plasma with a solid contact surface, the extended distal portion 616 of the long core 600 helps to diffuse any turbulent or shearing forces that propagate from the collection chamber 530 and into the separation chamber 325. Furthermore, by stabilizing the component layers and diffusing any turbulent or shearing forces, the long core 600 may increase collection efficiency and the quality of the collected plasma (e.g., less cellular components mix with the plasma).

Although the cores 500/600 described above have a number of ribs 540/640 that position the cores 500/600 within the bowl 300, other embodiments of the plasmapheresis bowl 300 may utilize cores with different structures. For example, as shown in FIGS. 12A-12C, some embodiments of the core (e.g., core 700) can include a ring 740 that is concentric with the tubular body 710 of the core 700. In a similar manner to the various surfaces of the ribs 540/640, the bottom surface 742 of the ring 740 may interface with the mating ledge 317 on the bowl body 310, the outer surface 744 of the ring 740 may interface with the interior face 318 of the neck portion 316 of the bowl 300, and the top surface 746 of the ring 740 may interface with the seal crown 356 on the header assembly 355.

To allow fluid/plasma to pass between the ring 740 and the tubular body 710 (e.g., so that it may flow up and over the proximal portion 712 and into the collection chamber 530), the core 700 may include spacers 755 that are spaced about the tubular body 712. The spacers 755 space the ring 740 from the tubular body 710 and provide flow paths 750 between the ring 740 and tubular body 710. It should be noted that, although the ring 740 is shown on a "long" version of the core, the ring 740 can also be utilized on the shorter core (e.g., like those shown in FIGS. 8A-8E) or a core having a length between the long and short core versions.

It is important to note that, although the various embodiments discussed above are in relation to a blood processing system that collects plasma, the features discussed herein may be applied to any type of blood processing system. For example, the features described herein may be implemented on blood processing systems that collect and/or process red blood cells, platelets and/or white blood cells.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A core for a plasmapheresis bowl comprising:
a cylindrical body defining the core and an interior of the core;
a ledge located within the interior of the core between a proximal end and a distal end of the cylindrical body, the ledge extending radially inward from an inner diameter of the core and having a top surface that defines, at least partially, a collection chamber within the plasmapheresis bowl; and
a plurality of ribs located on and spaced about a proximal portion of the cylindrical body, the plurality of ribs extending above the proximal end of the cylindrical body, thereby creating flow paths between each of the plurality of ribs, the flow paths allowing fluid to enter the interior of the cylindrical body and the collection chamber.

2. The core according to claim 1, wherein the cylindrical body has a second portion located below the ledge, at least a portion of the second portion configured to provide a reflective surface for an optical sensor.

3. The core according to claim 2, wherein the cylindrical body has a distal portion located below the second portion, the distal portion configured to stabilize fluid within the plasmapheresis bowl.

4. The core according to claim 1, wherein the proximal portion is located above the ledge, the proximal portion configured to isolate the collection chamber from a separation region within the plasmapheresis bowl.

5. The core according to claim 4, wherein the proximal portion is configured to prevent turbulence and shear forces within the collection chamber from reaching the separation region.

6. The core according to claim 4, wherein an inner wall of the proximal portion defines a side wall of the collection chamber.

7. The core according to claim 1, wherein each of the plurality of ribs includes a top surface, the top surface of at least one of the plurality of ribs configured to interface with a portion of the plasmapheresis bowl to secure the cylindrical body within the plasmapheresis bowl.

8. The core according to claim 1, wherein each of the plurality of ribs includes a bottom surface, the bottom surface of at least one of the plurality of ribs configured to interface with a mating ledge on a body of the plasmapheresis bowl, thereby locating the core in the plasmapheresis bowl.

9. The core according to claim 1, wherein each of the plurality of ribs includes an outer surface, the outer surface of at least one of the plurality of ribs configured to interface with an interior surface of the plasmapheresis bowl and create an interference fit between the core and the plasmapheresis bowl.

10. The core according to claim 9, wherein the interior surface of the plasmapheresis bowl is within a neck portion of the plasmapheresis bowl.

11. The core according to claim 1, wherein the top surface of the ledge slopes downward toward the distal end of the cylindrical body.

12. The core according to claim 1, wherein the ledge includes a bottom surface, the bottom surface of the ledge configured to prevent fluid within the interior of the core and below the ledge from entering the collection chamber.

13. The core according to claim 1, wherein the ledge includes an opening extending therethrough, the opening configured to allow a feed tube of the plasmapheresis bowl to pass through the ledge and allow fluid within the collection chamber to exit the collection chamber when the plasmapheresis bowl is stopped.

14. The core according to claim 13, wherein the opening is located at the center of the ledge such that it is coaxial with the cylindrical body.

15. The core according to claim 1, wherein the cylindrical body has a constant outer diameter along a length of the cylindrical body.

16. The core according to claim 1, wherein the plurality of ribs includes three or more ribs.

17. The core according to claim 1, wherein the plurality of ribs includes eight ribs.

18. The plasmapheresis bowl comprising:
an outer body rotatable about a longitudinal axis of the plasmapheresis bowl, the outer body having a main body defining an interior cavity, a neck portion extending proximal to the main body, and a shoulder connecting the main body and the neck portion;
a core located within and rotatable with the outer body, the core having:
a cylindrical body defining the core and an interior of the core,
a ledge located within the interior of the core between a proximal end and a distal end of the cylindrical body, the ledge extending radially inward from an inner diameter of the core and having a top surface that defines, at least partially, a collection chamber within the plasmapheresis bowl,
a plurality of ribs located on and spaced about a proximal portion of the cylindrical body, the plurality of ribs extending above the proximal end of the cylindrical body, thereby creating flow paths between each of the plurality of ribs, the flow paths allowing fluid to enter the interior of the cylindrical body and collection chamber;
a separation region located between the core and the outer body, rotation of the plasmapheresis bowl separating the whole blood within the separation region into a first blood component and a second blood component;
an inlet port for introducing whole blood into the plasmapheresis bowl;
a feed tube fluidly connected to and extending distally from the inlet port toward the bottom of the outer body, the feed tube configured to introduce the whole blood into the plasmapheresis bowl;
an outlet port for extracting a first blood component out of the plasmapheresis bowl; and
a rotary seal fluidly coupling the inlet port and outlet port to the outer body.

19. The plasmapheresis bowl according to claim 18, wherein the cylindrical body has a second portion located below the ledge, at least a portion of the second portion configured to provide a reflective surface for an optical sensor.

20. The plasmapheresis bowl according to claim 19, wherein the cylindrical body has a distal portion located below the second portion, the distal portion configured to stabilize fluid within the plasmapheresis bowl.

21. The plasmapheresis bowl according to claim 20, wherein the distal portion of the cylindrical body is configured to stabilize a plasma layer within the separation region.

22. The plasmapheresis bowl according to claim 21, wherein an inner diameter of a separated plasma layer within the separation region contacts the distal portion of the cylindrical body.

23. The plasmapheresis bowl according to claim 18, wherein the proximal portion is located above the ledge, the proximal portion configured to isolate the collection chamber from the separation region.

24. The plasmapheresis bowl according to claim 23, wherein the proximal portion is configured to prevent turbulence and shear forces within the collection chamber from reaching the separation region.

25. The plasmapheresis bowl according to claim 23, wherein an inner wall of the proximal portion defines a side wall of the collection chamber.

26. The plasmapheresis bowl according to claim 18, wherein each of the plurality of ribs includes a top surface, the top surface of at least one of the plurality of ribs configured to interface with a portion of a seal crown to secure the cylindrical body within the plasmapheresis bowl.

27. The plasmapheresis bowl according to claim 18, wherein the outer body has a mating ledge within the neck portion and each of the plurality of ribs includes a bottom surface, the bottom surface of at least one of the plurality of ribs configured to interface with the mating ledge of the plasmapheresis bowl, thereby locating the core in the plasmapheresis bowl.

28. The plasmapheresis bowl according to claim 18, wherein each of the plurality of ribs includes an outer surface, the outer surface of at least one of the plurality of ribs configured to interface with an interior surface of the neck portion of the plasmapheresis bowl, thereby creating an interference fit between the core and the plasmapheresis bowl.

29. The plasmapheresis bowl according to claim 18, wherein the top surface of the ledge slopes downward toward the distal end of the cylindrical body.

30. The plasmapheresis bowl according to claim 18, wherein the ledge includes a bottom surface, the bottom surface of the ledge configured to prevent fluid within the interior of the core and below the ledge from entering the collection chamber.

31. The plasmapheresis bowl according to claim 18, wherein the ledge includes an opening extending therethrough, the feed tube extending through the opening.

32. The plasmapheresis bowl according to claim 31, wherein the opening is located at the center of the ledge such that it is coaxial with the cylindrical body.

33. The plasmapheresis bowl according to claim 18, wherein the cylindrical body has a constant outer diameter along a length of the cylindrical body.

34. The plasmapheresis bowl according to claim 18, wherein the plurality of ribs includes eight ribs.

35. The plasmapheresis bowl according to claim 18, wherein the feed tube includes:
   a tubular member extending between a proximal end and a distal end of the feed tube, the tubular member having a flow path extending therethrough, the flow path fluidly connecting the inlet port and the interior cavity of the plasmapheresis bowl; and
   a first skirt member extending radially outward from the tubular member, the first skirt member having a first surface generally perpendicular to the tubular member and an angled surface extending radially outward and distally from the first surface, the angled surface being smooth.

36. The plasmapheresis bowl according to claim 35, wherein the feed tube further includes:
   at least one spacing rib located on the first surface and configured to space the first skirt member from a second skirt member, thereby creating a fluid channel extending between the first skirt member and the second skirt member.

37. The plasmapheresis bowl according to claim 36, wherein the second skirt member is located on a header assembly of the plasmapheresis bowl.

38. The plasmapheresis bowl according to claim 36, wherein the at least one spacing rib has a first portion that extends along the first surface, and a second portion that extends proximally along at least a portion of the tubular member.

39. The plasmapheresis bowl according to claim 36, wherein the core and the first and second skirts are configured such that the distance between the inner diameter of the proximal portion of the core and the outer diameter of the first and second skirts is maximized.

40. The plasmapheresis bowl according to claim 36, wherein the at least one spacing rib includes three ribs.

41. The plasmapheresis bowl according to claim 40, wherein the three spacing ribs are equally spaced about the skirt member.

42. The plasmapheresis bowl according to claim 36, wherein the fluid channel fluidly connects the collection chamber and the outlet port.

43. The plasmapheresis bowl according to claim 35, further comprising an extension tube connected to the tubular member at the distal end and extending toward a bottom of the plasmapheresis bowl, such that fluid entering the plasmapheresis bowl is introduced nearer to the bottom of the plasmapheresis bowl.

* * * * *